(12) United States Patent
Pomper et al.

(10) Patent No.: US 9,884,132 B2
(45) Date of Patent: Feb. 6, 2018

(54) HOMOMULTIVALENT AND HETEROMULTIVALENT INHIBITORS OF PROSTATE SPECIFIC MEMBRANE ANTIGEN (PSMA) AND USES THEREOF

(71) Applicant: THE JOHNS HOPKINS UNIVERSITY, Baltimore, MD (US)

(72) Inventors: Martin G. Pomper, Baltimore, MD (US); Sangeeta Ray, Ellicott City, MD (US); Ronnie C. Mease, Fairfax, VA (US); Hassan Shallal, Baltimore, MD (US)

(73) Assignee: THE JOHNS HOPKINS UNIVERSITY, Baltimore, MD (US)

(*) Notice: Subject to any disclaimer, the term of this patent is extended or adjusted under 35 U.S.C. 154(b) by 0 days.

(21) Appl. No.: 15/187,274

(22) Filed: Sep. 8, 2016

(65) Prior Publication Data

US 2017/0049912 A1  Feb. 23, 2017

Related U.S. Application Data

(63) Continuation of application No. 14/362,011, filed as application No. PCT/US2012/067162 on Nov. 30, 2012, now Pat. No. 9,371,360.

(60) Provisional application No. 61/565,179, filed on Nov. 30, 2011.

(51) Int. Cl.
| | |
|---|---|
| A61K 51/08 | (2006.01) |
| C07K 5/02 | (2006.01) |
| C07K 5/09 | (2006.01) |
| A61K 38/06 | (2006.01) |
| A61K 45/06 | (2006.01) |
| C07D 249/04 | (2006.01) |
| C07K 5/097 | (2006.01) |
| A61K 51/04 | (2006.01) |
| A61K 38/00 | (2006.01) |

(52) U.S. Cl.
CPC ............ *A61K 51/088* (2013.01); *A61K 38/06* (2013.01); *A61K 45/06* (2013.01); *C07D 249/04* (2013.01); *C07K 5/0217* (2013.01); *C07K 5/0815* (2013.01); *C07K 5/0821* (2013.01); *A61K 38/00* (2013.01); *A61K 51/0482* (2013.01)

(58) Field of Classification Search
CPC .................................. A61K 45/06; A61K 51/00
See application file for complete search history.

(56) References Cited

U.S. PATENT DOCUMENTS

| 7,408,079 B2 * | 8/2008 | Pomper ................ C07C 275/24 560/171 |
|---|---|---|
| 2009/0175794 A1 | 7/2009 | Zimmerman et al. |
| 2010/0178246 A1 | 7/2010 | Babich et al. |
| 2011/0064657 A1 | 3/2011 | Pomper et al. |
| 2011/0142760 A1 | 6/2011 | Pomper et al. |

OTHER PUBLICATIONS

European Search Report dated Nov. 10, 2016 from related European Patent Application No. 12853926.9.
Chinese Office Action dated May 6, 2015 from related Chinese Patent Application No. 2012800681632.
European Search Report dated Jun. 1, 2015 from related European Patent Application No. 12853926.
Huisgen, Angew Chem Int Ed. Oct. 1963, vol. 2, No. 10, pp. 565-598.
Rostovtsev et al., "A Stepwise Huisgen Cycloaddition Process: Copper(I)-Catalyzed Regioselective 'Ligation' of Azides and Terminal Alkynes", Angewandte Chemie (Int Ed) 2002; vol. 41, No. 14, pp. 2596-2599.
International Search Report dated Apr. 1, 2013 from PCT International Application No. PCT/US2012/067162.

* cited by examiner

*Primary Examiner* — Michael G Hartley
*Assistant Examiner* — Jagadishwar Samala
(74) *Attorney, Agent, or Firm* — Michael Best & Friedrich LLP; Jeffrey W. Childers

(57) ABSTRACT

The present invention provides bivalent and multivalent ligands with a view to improving the affinity and pharmacokinetic properties of a urea class of PSMA inhibitors. The compounds and their synthesis can be generalized to multivalent compounds of other target antigens. Because they present multiple copies of the pharmacophore, multivalent ligands can bind to receptors with high avidity and affinity, thereby serving as powerful inhibitors. The modular multivalent scaffolds of the present invention, in one or more embodiments, contains a lysine-based ($\alpha$, $\epsilon$-) dialkyne residue for incorporating two or more antigen binding moieties, such as PSMA binding Lys-Glu urea moieties, exploiting click chemistry and one or more additional lysine residues for subsequent modification with an imaging and/or therapeutic nuclides or a cytotoxic ligands for tumor cell killing.

13 Claims, 5 Drawing Sheets

HOMOMULTIVALENT AND HETEROMULTIVALENT INHIBITORS OF PROSTATE SPECIFIC MEMBRANE ANTIGEN (PSMA) AND USES THEREOF

CROSS-REFERENCE TO RELATED APPLICATIONS

This application is a continuation application of U.S. application Ser. No. 14/362,011 filed May 30, 2014, which is a 35 U.S.C. §371 U.S. national phase entry of International Application No. PCT/US2012/067162 having an international filing date of Nov. 30, 2012, which claims the benefit of U.S. Provisional Application No. 61/565,179, filed on Nov. 30, 2011, the contents of which are hereby incorporated by reference for all purposes as if fully set forth herein.

STATEMENT OF GOVERNMENTAL INTEREST

This invention was made with U.S. government support under grant nos. 5RO1CA134675-03 and 1K25CA148901-01A1. The U.S. government has certain rights in the invention.

BACKGROUND OF THE INVENTION

Prostate cancer (PCa) will kill an estimated 33,720 men in the US alone this year. The integral membrane protein prostate-specific membrane antigen (PSMA) is becoming increasingly recognized as a viable target for imaging and therapy of prostate and other forms of cancer. PSMA is significantly over-expressed in PCa and metastases, particularly with respect to the castration-resistant form. Accordingly, PSMA may provide a negative prognostic indicator for PCa—enabling distinction of indolent from aggressive disease. Imaging PSMA has also provided insight into androgen signaling and information on response to taxane therapy.

Recently the present inventors and others have demonstrated successful PSMA-targeted radionuclide imaging in experimental models of PCa using cysteine-glutamate or lysine-glutamate ureas. With those agents the radionuclide ($^{11}$C, $^{125}$I, $^{18}$F) is attached to the cysteine or lysine moiety via a small prosthetic group. For large molecular fragments, such as radiometal ($^{99m}$Tc, $^{68}$Ga, $^{111}$In) chelators, organic fluorescent molecules, and nanoparticles, we have determined that a linking moiety of at least 20 Å (long-linker) between the large molecule and the lysine moiety facilitates productive binding. We have also developed a PSMA-targeted, dual (radionuclide and optical) modality imaging platform that enables sequential, dual modality imaging.

Various approaches have been reported to exploit multivalent scaffolds for the construction of molecular imaging probes. However, the chemistry used to produce them can become complicated, even more so when a bifunctional chelator must be attached to a separately multimerized construct to introduce a radionuclide, for example, for imaging. Although, the concept of multimerization for PSMA targeted, near-infrared imaging agents has been proffered for in vitro cell binding studies, to our knowledge a multivalent PSMA-binding agent has not yet been shown to image PSMA successfully in vivo.

Therefore, there still exists a need to provide better and more convenient methods for creating scaffolds for multimeric presentation of PSMA and other targeting species including bivalent and multivalent forms, over the corresponding monomer, to target antigens in vivo.

SUMMARY OF THE INVENTION

In accordance with one or more embodiments, the present invention provides bivalent and multivalent ligands with a view to improving the affinity and pharmacokinetic properties of a urea class of PSMA inhibitors. The strategy we employ can be generalized to multivalent compounds of other target antigens. Because they present multiple copies of the pharmacophore, multivalent ligands can bind to receptors with high avidity and affinity, thereby serving as powerful inhibitors.

The modular multivalent scaffolds of the present invention, in one or more embodiments, contains a lysine-based ($\alpha$-, $\epsilon$-) dialkyne residue for incorporating PSMA binding Lys-Glu urea moieties exploiting click chemistry and one or more additional lysine residues for subsequent modification with an imaging and/or therapeutic nuclides or a cytotoxic ligands for tumor cell killing.

In embodiment, the divalent agent has a prolonged biological half-life and enhanced specific binding and retention in tissues expressing PSMA.

In accordance with an embodiment, the present invention provides a compound of formula I:

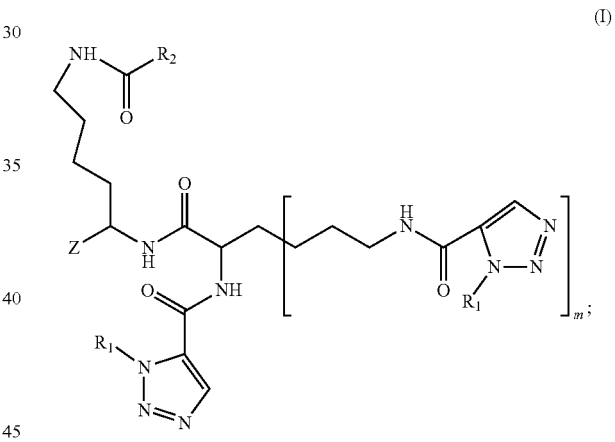

(I)

wherein Z is H, $CO_2H$, $NH_2$, SH and OH;
wherein m is 2 to 16;
wherein $R_1$ is the same or different moiety and is a compound of formula VII:

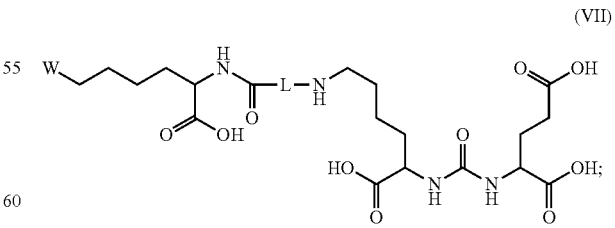

(VII)

wherein W is $C_1$ to $C_{10}$ alkyl, alkylamino, alkyl, alkylamino, alkenyl, alkynyl, hydroxyalkyl, alkoxy, dialkylamino thioalkyl, thioalkenyl, thioalkynyl, aryloxy, acyloxy, thioacyl, amido, and sulphonamido; wherein each of alkyl, or aryl moiety may be unsubstituted or substituted with one or more substituents selected from the group consisting of halo, hydroxy, carboxy, phosphoryl, phosphonyl, phosphono $C_1$-$C_6$ alkyl, carboxy $C_1$-$C_6$ alkyl, dicarboxy $C_1$-$C_6$ alkyl, dicarboxy halo $C_1$-$C_6$ alkyl, sulfonyl, cyano, nitro, alkoxy, alkylthio, acyl, acyloxy, thioacyl, acylthio, aryloxy, amino, alkylamino, dialkylamino, trialkylamino, arylalkylamino, guanidino, aldehydo, ureido, and aminocarbonyl; W may be substituted with a chelating moiety, a fluorescent dye or H, wherein when W is a chelating moiety, it can be bound to a metal ion useful in imaging, or as a cytotoxic moiety; and L is a linker, wherein the linker is a $C_8$ to $C_{20}$ alkyl, alkylamino, alkenyl, alkynyl, hydroxyalkyl, alkoxy, dialkylamino thioalkyl, thioalkenyl, thioalkynyl, aryloxy, acyloxy, thioacyl, amido, polyethylene glycol and sulphonamido, wherein each of alkyl or aryl moiety may be unsubstituted or substituted with one or more substituents selected from the group consisting of halo, hydroxy, carboxy, phosphoryl, phosphonyl, phosphono $C_1$-$C_6$ alkyl, carboxy $C_1$-$C_6$ alkyl, dicarboxy $C_1$-$C_6$ alkyl, dicarboxy halo $C_1$-$C_6$ alkyl, sulfonyl, cyano, nitro, alkoxy, alkylthio, acyl, acyloxy, thioacyl, acyl- In accordance with another embodiment, the present invention provides a compound of formula II:

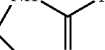

(II)

wherein Z is H, $CO_2H$, $NH_2$, SH and OH;
wherein $R_1$ is the same or different moiety and is selected from the group consisting of:

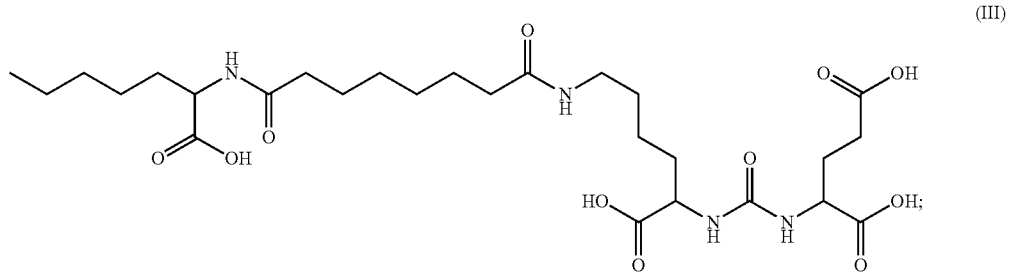

(III)

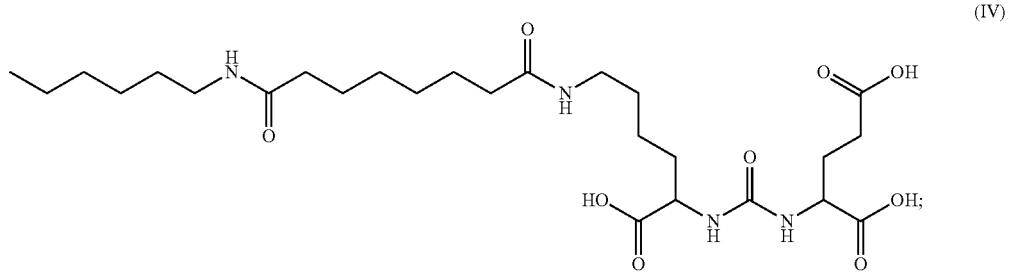

(IV)

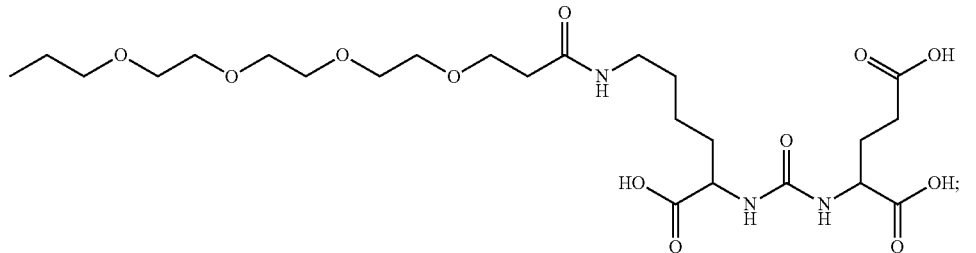

(V)

thio, aryloxy, amino, alkylamino, dialkylamino, trialkylamino, arylalkylamino, guanidino, aldehydo, ureido, and aminocarbonyl; and alternatively, $R_1$ is a peptide ligand to an enzyme or endothelial receptor, and wherein $R_2$ is a chelating moiety, a fluorescent dye or H, wherein when $R_2$ is a chelating moiety, it can be bound to a metal ion useful in imaging, or as a cytotoxic moiety; or a pharmaceutically acceptable salt, solvate, or stereoisomer thereof.

and alternatively, $R_1$ is a peptide ligand to an enzyme or endothelial receptor, and wherein $R_2$ is a chelating moiety, a fluorescent dye or H, wherein when $R_2$ is a chelating moiety, it can be bound to a metal ion useful in imaging, or as a cytotoxic moiety; or a pharmaceutically acceptable salt, solvate, or stereoisomer thereof.

In accordance with a further embodiment, the present invention provides a compound of formula VI:

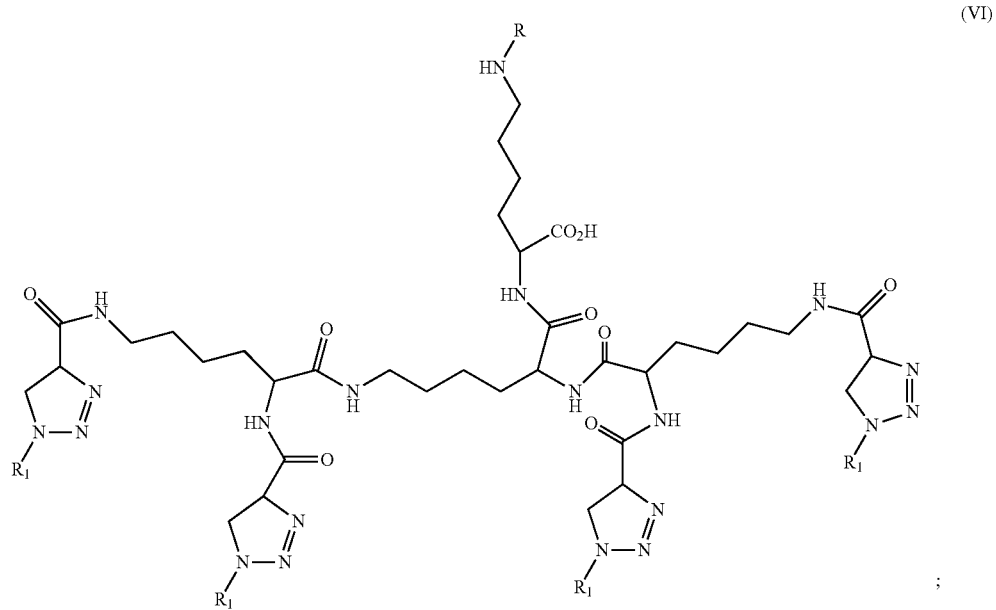

(VI)

wherein $R_1$ is the same or different moiety and is a compound of formula VI:

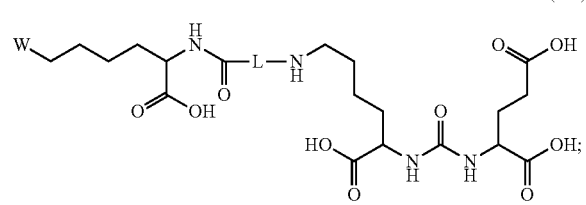

(VII)

wherein W is $C_1$ to $C_{10}$ alkyl, alkylamino, alkyl, alkylamino, alkenyl, alkynyl, hydroxyalkyl, alkoxy, dialkylamino thioalkyl, thioalkenyl, thioalkynyl, aryloxy, acyloxy, thioacyl, amido, and sulphonamido; wherein each of alkyl, or aryl moiety may be unsubstituted or substituted with one or more substituents selected from the group consisting of halo, hydroxy, carboxy, phosphoryl, phosphonyl, phosphono $C_1$-$C_6$ alkyl, carboxy $C_1$-$C_6$ alkyl, dicarboxy $C_1$-$C_6$ alkyl, dicarboxy halo $C_1$-$C_6$ alkyl, sulfonyl, cyano, nitro, alkoxy, alkylthio, acyl, acyloxy, thioacyl, acylthio, aryloxy, amino, alkylamino, dialkylamino, trialkylamino, arylalkylamino, guanidino, aldehydo, ureido, and aminocarbonyl; W may be substituted with a chelating moiety, a fluorescent dye or H, wherein when W is a chelating moiety, it can be bound to a metal ion useful in imaging, or as a cytotoxic moiety; and L is a linker, wherein the linker is a $C_8$ to $C_{20}$ alkyl, alkylamino, alkenyl, alkynyl, hydroxyalkyl, alkoxy, dialkylamino thioalkyl, thioalkenyl, thioalkynyl, aryloxy, acyloxy, thioacyl, amido, polyethylene glycol and sulphonamido, wherein each of alkyl or aryl moiety may be unsubstituted or substituted with one or more substituents selected from the group consisting of halo, hydroxy, carboxy, phosphoryl, phosphonyl, phosphono $C_1$-$C_6$ alkyl, carboxy $C_1$-$C_6$ alkyl, dicarboxy $C_1$-$C_6$ alkyl, dicarboxy halo $C_1$-$C_6$ alkyl, sulfonyl, cyano, nitro, alkoxy, alkylthio, acyl, acyloxy, thioacyl, acylthio, aryloxy, amino, alkylamino, dialkylamino, trialkylamino, arylalkylamino, guanidino, aldehydo, ureido, and aminocarbonyl; and alternatively, $R_1$ is a peptide ligand to an enzyme or endothelial receptor, and wherein R is a chelating moiety, a fluorescent dye or H, wherein when R is a chelating moiety, it can be bound to a metal ion useful in imaging, or as a cytotoxic moiety; or a pharmaceutically acceptable salt, solvate, or stereoisomer thereof.

In accordance with still a further embodiment, the present invention provides a compound of formula V:

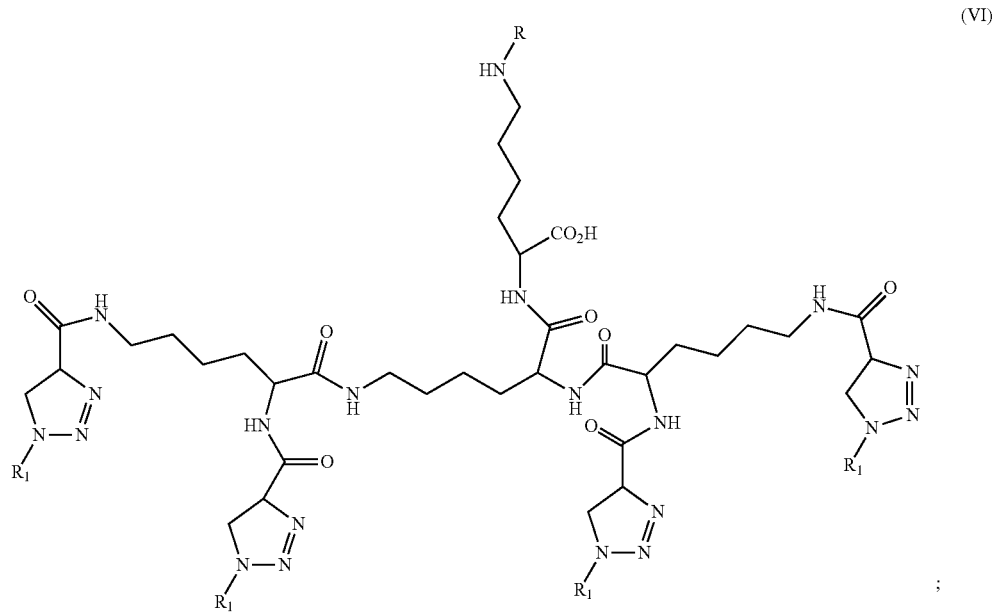
(VI)

wherein $R_1$ is the same or different moiety and is selected from the group consisting of:

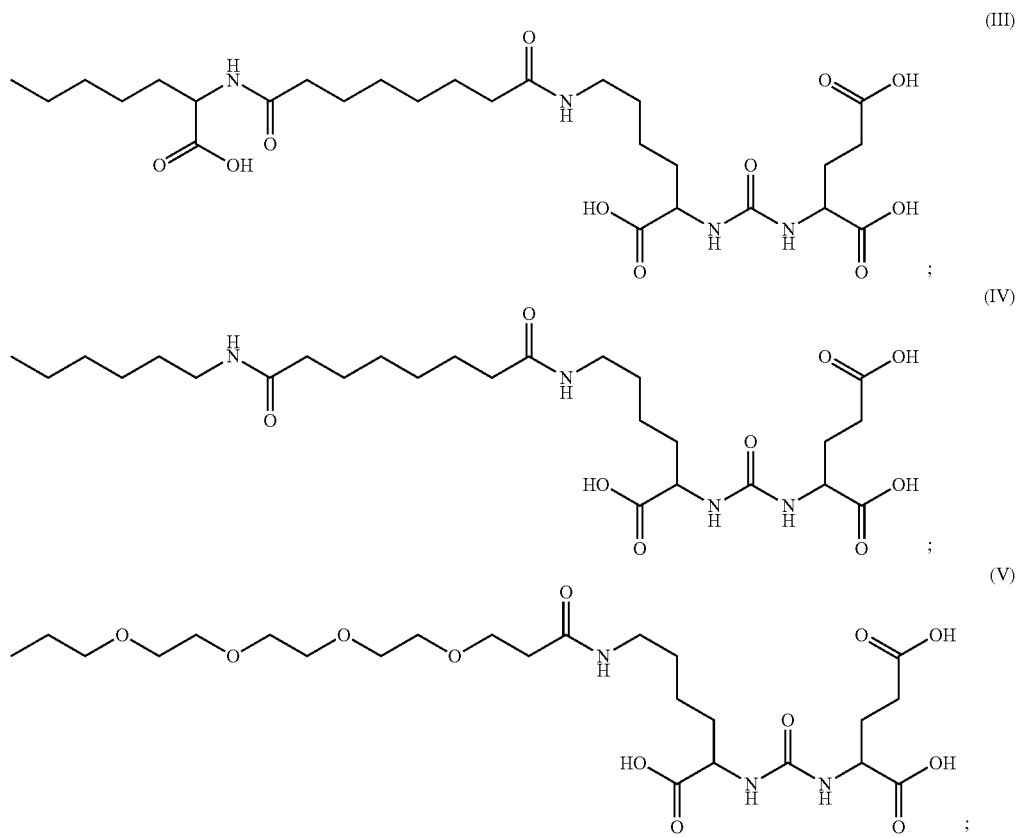

and alternatively, $R_1$ is a peptide ligand to an enzyme or endothelial receptor, and wherein R is a chelating moiety, a fluorescent dye or H, wherein when R is a chelating moiety, it can be bound to a metal ion useful in imaging, or as a cytotoxic moiety; or a pharmaceutically acceptable salt, solvate, or stereoisomer thereof.

In accordance with an embodiment, the present invention provides a pharmaceutical composition comprising a compound, salt, solvate, or stereoisomer of any one of the compounds described above, and a pharmaceutically acceptable carrier.

In accordance with an embodiment, the present invention provides a pharmaceutical composition comprising a compound, salt, solvate, or stereoisomer of any one of the compounds described above, and at least one or more other biologically active agents.

In accordance with an embodiment, the present invention provides a method of treating or preventing cancer in a subject comprising administering to the subject an effective amount of a compound, salt, solvate, or stereoisomer of any one of the compounds described above, or the pharmaceutical compositions described above.

In accordance with an embodiment, the present invention provides a method of imaging prostate cancer in a subject comprising administering to the subject an effective amount of a compound, salt, solvate, or stereoisomer of any one of the compounds described above, or the pharmaceutical compositions described above wherein R or $R_2$ is an metal ion or dye useful for imaging.

DETAILED DESCRIPTION OF THE INVENTION

Figure 1:
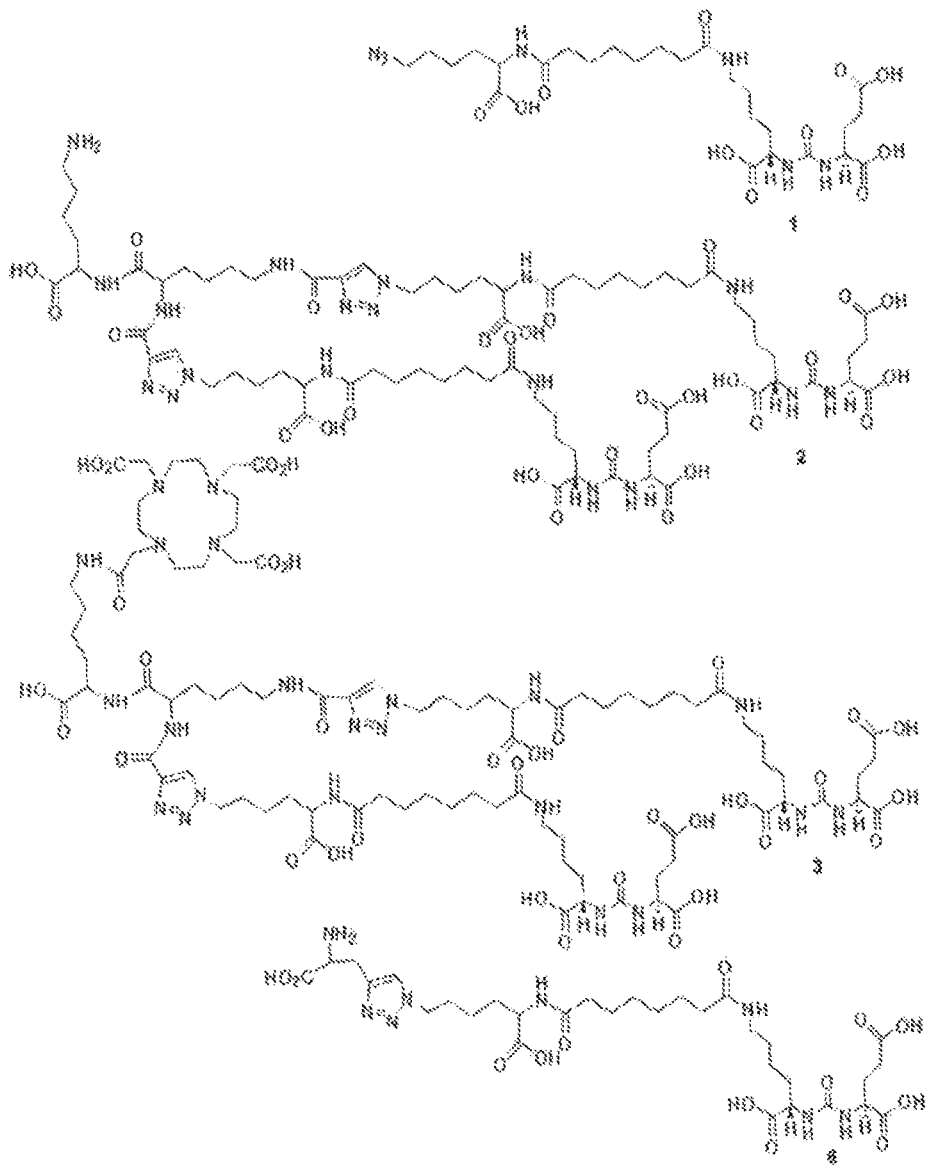
FIG. 1 depicts certain embodiments of the present invention.

The compositions and methods of the present invention described herein are able to be generalized to other modalities and for molecular radiotherapy. Since DOTA is a general chelating agent, compound 3 of the present invention may also be used with other radiometals such as $^{68}$Ga, $^{64}$Cu or $^{86}$Y for positron emission tomography (PET) or $^{90}$Y and $^{177}$Lu for therapy. Technetium-99m can also be incorporated by replacing DOTA with standard peptide-based chelating agents containing nitrogen and sulfur donors ($N_3S$, $N_2S_2$), the HYNIC chelator or by use of single amino acid chelating (SAAC) agents. Further attesting to its utility, the compounds of the present invention, such as bivalent compound 2 can also be used as a versatile intermediate for medically important nonmetals, such as the radiohalogenated imaging isotopes $^{18}$F, $^{123}$I or $^{211}$At/$^{131}$I for radiotherapy. Other fluorophores/chelating agents/radiometals/nonmetals/cytotoxic agent combinations can also be envisioned using this approach. Another significant aspect of the multivalent scaffold is that it enables the generation systematically of at least 4- and 8-valent, up to 16-valent urea compounds from the lysine-diamine intermediate 4 upon repeated conjugation of 4 with Fmoc-Lys(Fmoc-OH) to produce a lysine-based multimeric urea dendron.

In accordance with an embodiment, the present invention provides In accordance with an embodiment, the present invention provides a compound of formula I:

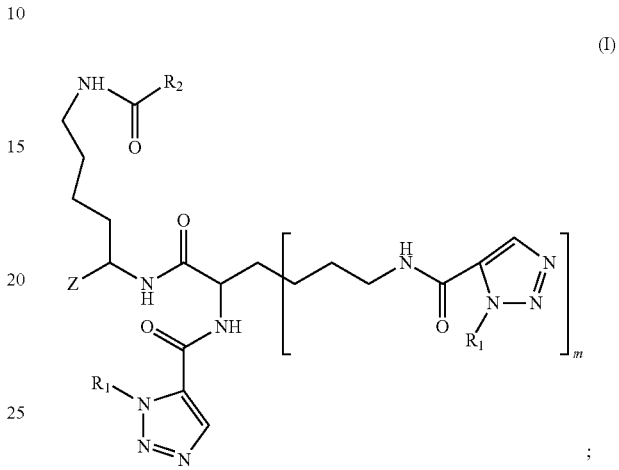

wherein Z is H, $CO_2H$, $NH_2$, SH and OH;
wherein m is 2 to 16;
wherein $R_1$ is the same or different moiety and is a compound of formula VI:

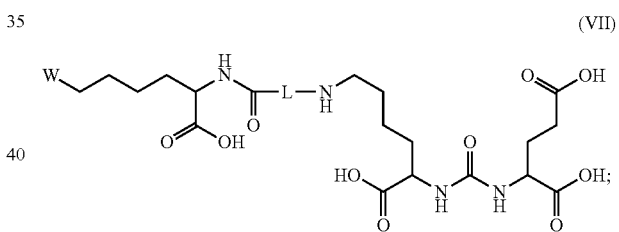

wherein W is $C_1$ to $C_{10}$ alkyl, alkylamino, alkyl, alkylamino, alkenyl, alkynyl, hydroxyalkyl, alkoxy, dialkylamino thioalkyl, thioalkenyl, thioalkynyl, aryloxy, acyloxy, thioacyl, amido, and sulphonamido; wherein each of alkyl, or aryl moiety may be unsubstituted or substituted with one or more substituents selected from the group consisting of halo, hydroxy, carboxy, phosphoryl, phosphonyl, phosphono $C_1$-$C_6$ alkyl, carboxy $C_1$-$C_6$ alkyl, dicarboxy $C_1$-$C_6$ alkyl, dicarboxy halo $C_1$-$C_6$ alkyl, sulfonyl, cyano, nitro, alkoxy, alkylthio, acyl, acyloxy, thioacyl, acylthio, aryloxy, amino, alkylamino, dialkylamino, trialkylamino, arylalkylamino, guanidino, aldehydo, ureido, and aminocarbonyl; W may be substituted with a chelating moiety, a fluorescent dye or H, wherein when W is a chelating moiety, it can be bound to a metal ion useful in imaging, or as a cytotoxic moiety; and L is a linker, wherein the linker is a $C_8$ to $C_{20}$ alkyl, alkylamino, alkenyl, alkynyl, hydroxyalkyl, alkoxy, dialkylamino thioalkyl, thioalkenyl, thioalkynyl, aryloxy, acyloxy, thioacyl, amido, polyethylene glycol and sulphonamido, wherein each of alkyl or aryl moiety may be unsubstituted or substituted with one or more substituents selected from the group consisting of halo, hydroxy, carboxy, phosphoryl, phosphonyl, phosphono $C_1$-$C_6$ alkyl, carboxy $C_1$-$C_6$ alkyl, dicarboxy $C_1$-$C_6$ alkyl, dicarboxy halo $C_1$-$C_6$ alkyl, sulfonyl, cyano, nitro, alkoxy, alkylthio, acyl, acyloxy, thioacyl, acylthio, aryloxy, amino, alkylamino, dialkylamino, trialkylamino, arylalkylamino, guanidino, aldehydo, ureido, and aminocarbonyl; and alternatively, $R_1$ is a peptide ligand to an enzyme or endothelial receptor, and wherein $R_2$ is a chelating moiety, a fluorescent dye or H, wherein when $R_2$ is a chelating moiety, it can be bound to a metal ion useful in imaging, or as a cytotoxic moiety; or a pharmaceutically acceptable salt, solvate, or stereoisomer thereof.

In one or more embodiments, L is a linker selected from the group consisting of:

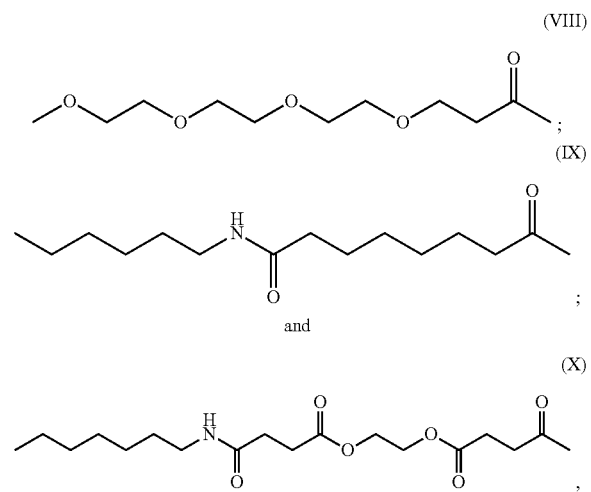

As used herein, examples of the term "alkyl" preferably include a $C_{1-6}$ alkyl (e.g., methyl, ethyl, propyl, isopropyl, butyl, isobutyl, sec-butyl, tert-butyl, pentyl, hexyl, etc.) and the like.

As used herein, examples of the term "alkenyl" preferably include $C_{2-6}$ alkenyl (e.g., vinyl, allyl, isopropenyl, 1-butenyl, 2-butenyl, 3-butenyl, 2-methyl-2-propenyl, 1-methyl-2-propenyl, 2-methyl-1-propenyl, etc.) and the like.

As used herein, examples of the term "alkynyl" preferably include $C_{2-6}$ alkynyl (e.g., ethynyl, propargyl, 1-butynyl, 2-butynyl, 3-butynyl, 1-hexynyl, etc.) and the like.

Examples of the term "cycloalkyl" preferably include a $C_{3-8}$ cycloalkyl (e.g., a cyclopropyl, cyclobutyl, cyclopentyl, cyclohexyl, etc.) and the like.

Examples of the term "aryl" preferably include a $C_{6-14}$ aryl (e.g., a phenyl, 1-naphthyl, a 2-naphthyl, 2-biphenylyl group, 3-biphenylyl, 4-biphenylyl, 2-anthracenyl, etc.) and the like.

Examples of the term "arylalkyl" preferably include a $C_{6-14}$ arylalkyl (e.g., benzyl, phenylethyl, diphenylmethyl, 1-naphthylmethyl, 2-naphthylmethyl, 2,2-diphenylethyl, 3-phenylpropyl, 4-phenylbutyl, 5-phenylpentyl, etc.) and the like.

The term "hydroxyalkyl" embraces linear or branched alkyl groups having one to about ten carbon atoms any one of which may be substituted with one or more hydroxyl groups.

The term "alkylamino" includes monoalkylamino. The term "monoalkylamino" means an amino, which is substituted with an alkyl as defined herein. Examples of monoalkylamino substituents include, but are not limited to, methylamino, ethylamino, isopropylamino, t-butylamino, and the like. The term "dialkylamino" means an amino, which is substituted with two alkyls as defined herein, which alkyls can be the same or different. Examples of dialkylamino substituents include dimethylamino, diethylamino, ethylisopropylamino, diisopropylamino, dibutylamino, and the like.

The terms "alkylthio," "alkenylthio" and "alkynylthio" mean a group consisting of a sulphur atom bonded to an alkyl-, alkenyl- or alkynyl-group, which is bonded via the sulphur atom to the entity to which the group is bonded.

Accordingly, included within the compounds of the present invention are the tautomeric forms of the disclosed compounds, isomeric forms including enantiomers, stereoisomers, and diastereoisomers, and the pharmaceutically-acceptable salts thereof. The term "pharmaceutically acceptable salts" embraces salts commonly used to form alkali metal salts and to form addition salts of free acids or free bases. Examples of acids which may be employed to form pharmaceutically acceptable acid addition salts include such inorganic acids as hydrochloric acid, sulphuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. Suitable pharmaceutically acceptable salts of the compounds of the present invention include, for example, acid addition salts which may, for example, be formed by mixing a solution of the compound according to the invention with a solution of a pharmaceutically acceptable acid, such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. All of these salts may be prepared by conventional means by reacting, for example, the appropriate acid or base with the corresponding compounds of the present invention.

Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicines, the salts of the compounds of the present invention should be pharmaceutically acceptable salts. Other salts may, however, be useful in the preparation of the compounds according to the invention or of their pharmaceutically acceptable salts.

In addition, embodiments of the invention include hydrates of the compounds of the present invention. The term "hydrate" includes but is not limited to hemihydrate, monohydrate, dihydrate, trihydrate and the like. Hydrates of the compounds of the present invention may be prepared by contacting the compounds with water under suitable conditions to produce the hydrate of choice.

As defined herein, in one or more embodiments, "contacting" means that the one or more compounds of the present invention are introduced into a sample having at least one cancer cell expressing PSMA, and appropriate enzymes or reagents, in a test tube, flask, tissue culture, chip, array, plate, microplate, capillary, or the like, and incubated at a temperature and time sufficient to permit binding of the at least one compound to the PSMA of the cancer cell. Methods for contacting the samples with the compounds, and other specific binding components are known to those skilled in the art, and may be selected depending on the type of assay protocol to be run. Incubation methods are also standard and are known to those skilled in the art.

In another embodiment, the term "contacting" means that the at least one compound of the present invention is introduced into a subject, preferably a subject receiving treatment for a PSMA related disorder, such as prostate cancer, and the at least one compounds is allowed to come in contact with the PSMA in vivo.

Embodiments of the invention also include a process for preparing pharmaceutical products comprising the compounds. The term "pharmaceutical product" means a composition suitable for pharmaceutical use (pharmaceutical composition), as defined herein. Pharmaceutical compositions formulated for particular applications comprising the compounds of the present invention are also part of this invention, and are to be considered an embodiment thereof.

As used herein, the term "treat," as well as words stemming therefrom, includes preventative as well as disorder remitative treatment. The terms "reduce," "suppress," "prevent," and "inhibit," as well as words stemming therefrom, have their commonly understood meaning of lessening or decreasing. These words do not necessarily imply 100% or complete treatment, reduction, suppression, or inhibition.

With respect to pharmaceutical compositions described herein, the pharmaceutically acceptable carrier can be any of those conventionally used, and is limited only by physico-chemical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. Examples of the pharmaceutically acceptable carriers include soluble carriers such as known buffers which can be physiologically acceptable (e.g., phosphate buffer) as well as solid compositions such as solid-state carriers or latex beads. It is preferred that the pharmaceutically acceptable carrier be one which is chemically inert to the active agent(s), and one which has little or no detrimental side effects or toxicity under the conditions of use.

The carriers or diluents used herein may be solid carriers or diluents for solid formulations, liquid carriers or diluents for liquid formulations, or mixtures thereof.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be, for example, aqueous or non-aqueous solutions, suspensions, emulsions or oils. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Examples of oils are those of petroleum, animal, vegetable, or synthetic origin, for example, peanut oil, soybean oil, mineral oil, olive oil, sunflower oil, fish-liver oil, sesame oil, cottonseed oil, corn oil, olive, petrolatum, and mineral. Suitable fatty acids for use in parenteral formulations include, for example, oleic acid, stearic acid, and isostearic acid. Ethyl oleate and isopropyl myristate are examples of suitable fatty acid esters.

Parenteral vehicles (for subcutaneous, intravenous, intraarterial, or intramuscular injection) include, for example, sodium chloride solution, Ringer's dextrose, dextrose and sodium chloride, lactated Ringer's and fixed oils. Formulations suitable for parenteral administration include, for example, aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Intravenous vehicles include, for example, fluid and nutrient replenishes, electrolyte replenishes such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions.

In addition, in an embodiment, the compounds of the present invention may further comprise, for example, binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., crcmophor, glycerol, polyethylene glycerol, benzalkonium chloride, benzyl benzoate, cyclodextrins, sorbitan esters, stearic acids), anti-oxidants (e.g., ascorbic acid, sodium metabisulfite, butylated hydroxyanisole), stabilizers (e.g., hydroxypropyl cellulose, hydroxypropyl methyl cellulose), viscosity increasing agents (e.g., carbomer, colloidal silicon dioxide, ethyl cellulose, guar gum), sweeteners (e.g., aspartame, citric acid), preservatives (e.g., thimerosal, benzyl alcohol, parabens), lubricants (e.g., stearic acid, magnesium sterate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates), and/or adjuvants.

The choice of carrier will be determined, in part, by the particular compound, as well as by the particular method used to administer the compound. Accordingly, there are a variety of suitable formulations of the pharmaceutical composition of the invention. The following formulations for parenteral, subcutaneous, intravenous, intramuscular, intraarterial, intrathecal and interperitoneal administration are exemplary, and are in no way limiting. More than one route can be used to administer the compounds, and in certain instances, a particular route can provide a more immediate and more effective response than another route.

Suitable soaps for use in parenteral formulations include, for example, fatty alkali metal, ammonium, and triethanolamine salts, and suitable detergents include, for example, (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the compounds in solution. Preservatives and buffers may be used. In order to minimize or eliminate irritation at the site of injection, such compositions may contain one or more nonionic surfactants, for example, having a hydrophile-lipophile balance (HLB) of from about 12 to about 17. The quantity of surfactant in such formulations will typically range from about 5% to about 15% by weight. Suitable surfactants include, for example, polyethylene glycol sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose scaled containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Injectable formulations are in accordance with the invention. The requirements for effective pharmaceutical carriers for injectable compositions are well-known to those of ordinary skill in the art (see, e.g., *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Trissel, 15th ed., pages 622-630 (2009)).

For purposes of the invention, the amount or dose of the compounds, salts, solvates, or stereoisomers of any one the compounds of Formula I, as set forth above, administered should be sufficient to effect, e.g., a therapeutic or prophylactic response, in the subject over a reasonable time frame. The dose will be determined by the efficacy of the particular compound and the condition of a human, as well as the body weight of a human to be treated.

The dose of the compounds, salts, solvates, or stereoisomers of any one the compounds of Formula I, as set forth above, of the present invention also will be determined by the existence, nature and extent of any adverse side effects that might accompany the administration of a particular compound. Typically, an attending physician will decide the dosage of the compound with which to treat each individual patient, taking into consideration a variety of factors, such as age, body weight, general health, diet, sex, compound to be administered, route of administration, and the severity of the condition being treated. By way of example, and not intending to limit the invention, the dose of the compound can be about 0.001 to about 1000 mg/kg body weight of the subject being treated/day, from about 0.01 to about 100 mg/kg body weight/day, about 0.1 mg to about 10 mg/kg body weight/day.

Radionuclides are generally classified as either being diagnostic or therapeutic in their application. Although diagnostic imaging agents have historically been a mainstay in the nuclear pharmacy industry, during the past decade there has been increased interest in the development and use of radiotherapeutic imaging agents. This shift in focus has been elicited primarily from research involving combining radioactive radionuclides with sophisticated molecular earners. Because of radiation's damaging effect on tissues, it is important to target the bio distribution of radiopharmaceuticals as accurately as possible. Generally speaking, PET uses imaging agents labeled with the positron-emitters such as 18F, $^{11}$C, $^{13}$N and $^{15}$O, $^{75}$Br, $^{76}$Br and $^{124}$I, SPECT uses imaging agents labeled with the single-photon-emitters such as $^{201}$Tl, 99mTc, $^{123}$I, $^{111}$In and $^{131}$I.

Alpha-particle emitter radiopharmaceutical therapy (RPT) uses alpha-emitting radionuclides to kill the targeted cell or population of cells. Examples of such alpha emitters include, for example, $^{213}$Bi labeled agents and $^{225}$Ac labeled agents, for example.

As used herein, the term "antigen" is defined as any polypeptide or fragment thereof which selectively binds to a particular cell type in a host through recognition of a cell-type specific (e.g. tumor cell or other host cell or population of cells) marker (e.g., antigen or receptor. In other embodiments, the term "antigen" can mean a protein receptor on a cell membrane. PSMA is an example of such a protein receptor antigen. The cell targeting moiety can be an antibody or peptide. Other proteins, enzymes and growth factors can also be targeting moieties. Targeting moieties can also be defined as an antibody or fragment thereof which selectively binds to a particular cell type in a host through recognition of a cell surface antigen. Preferred cell targeting antibodies are specific for solid tumors and cancer cells. Most preferred is PSMA for use in prostate cancers.

In an embodiment, the term "administering" means that the compounds of the present invention are introduced into a subject, preferably a subject receiving treatment for a disease, and the compounds are allowed to come in contact with the one or more disease related cells or population of cells in vivo. In some embodiments the host cell or population of cells in the host can be any cell or population of cells that can be selectively bound by the antigens bound to the compounds of formula I described above. One of ordinary skill in the art would understand the host cells can be cancer cells. In other embodiments, the host cell or population of cells could be immunological cells, such as B cells and T cells, or for example, other cells for which imaging or cytotoxic therapy is appropriate.

As used herein, the term "detection" "imaging" or "radiodetection" means the use of certain properties of isotopes and the energetic particles emitted from radioactive material to obtain pharmacokinetic information. In addition, the term "scintigraphy" means a diagnostic test in which a two-dimensional image of a body having a radiation source is obtained through the use of radioisotopes. A radioactive chemical is injected into the patient which then concentrates in the target cells or organ of interest. By placing a camera that senses radioactivity over the body, an image of the target cells or organ of interest can be created. The particles can be detected by suitable devices such as gamma cameras, positron emission tomography (PET) machines, single photon emission computed tomography (SPECT) machines and the like.

In some embodiments, the chelated metal is Tc, In, Ga, Y, Lu, Re, Cu, Ac, Bi, Pb, Sm, Sc, Co, Ho, Gd, Eu. Tb, or Dy. In some embodiments the metal is an isotope, for example a radioactive isotope. In some embodiments, the isotope is Tc-94m, Tc-99m, In-111, G-67, Ga-68, Y-86, Y-90, Lu-177, Re-186, Re-188, Cu-64, Cu-67, Co-55, Co-57, Sc-47, Ac-225, Bi-213, Bi-212, Pb-212, Sm-153, Ho-166, or Dy-166.

In some embodiments, $R_2$ is a fluorescent dye moiety (FG) that emits light in the visible or near infrared spectrum. FG includes any additional atoms or linkers necessary to attach the fluorescent dye moiety to the rest of the compound. For instance linking groups having alkyl, aryl, combination of alkyl and aryl, or alkyl and aryl groups having heteroatoms may be present in the chelating moiety, so long as the linker does not interfere with the fluorescence of the dye.

In some embodiments, the fluorescent dye moiety includes a poly(ethyleneglycol) linker. Numerous fluorescent dye moieties are known in the art, and will be readily apparent to one of ordinary skill. Many fluorescent dyes are commercially available with activated groups used to react with protein side chains or other compounds.

Examples of fluorescent compounds which may form all or part of the structure of FG of the present invention include carbocyanine, indocarbocyanine, oxacarbocyanine, thiacarbocyanine, merocyanine, polymethine, coumarine, rhodamine, xanthene, fluorescein, and boron-dipyrromethane (BODIPY) compounds, to name a few.

Examples of fluorescent dye moieties include those described in WO 20089/109832, which is incorporated by reference herein in its entirety.

Specific dyes that can be used with the compounds of the present invention, which emit in the near infrared spectrum include commercially available compounds Cy5, Cy5.5, and Cy7, available from GE Healthcare; VivoTag-680, VivoTag-S680, and VivoTag-S750, available from VisEn Medical; AlexaFiuor660, AlexaFiuor680, AlexaFiuor700, AlexaFiuor750, and AlexaFiuor790, available from Invitrogen; Dy677, Dy676, Dy682, Dy752, and Dy780, available from Dyonics; DyLight547, and Dylight647, available from Pierce; Hilyte Fluor 647, Hilyte Fluor 680, and Hilyte Fluor 750, available from AnaSpec; IRDye 800CW, IRDye BOORS, and IRDye 700DX, available from Li-Cor; and ADS780WS, ADS830WS, and ADS832WS, available from American Dye Source.

In accordance with another embodiment, the present invention provides a compound of formula II:

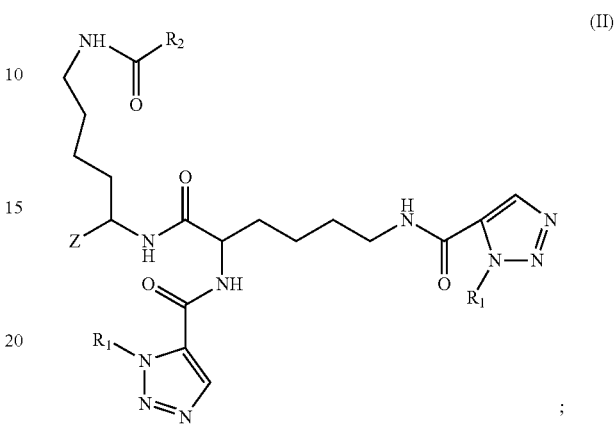

wherein Z is H, $CO_2H$, $NH_2$, SH and OH;
wherein $R_1$ is the same or different moiety and is selected from the group consisting of:

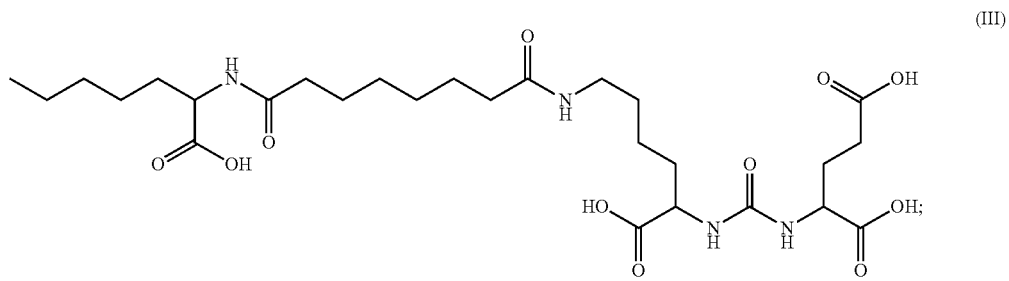

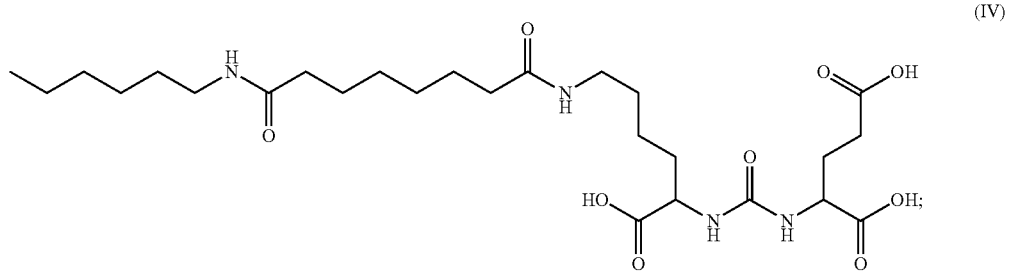

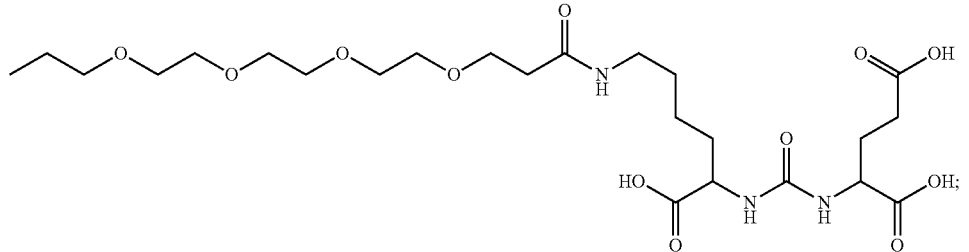

and alternatively, $R_1$ is a peptide ligand to an enzyme or endothelial receptor; and wherein $R_2$ is a chelating moiety, a fluorescent dye or H, wherein when $R_2$ is a chelating moiety, it can be bound to a metal ion useful in imaging, or as a cytotoxic moiety; or a pharmaceutically acceptable salt, solvate, or stereoisomer thereof.

As used herein, the term "peptide ligand" Ls meant to mean an antigen binding moiety which is specific for a known antigen, polypeptide or protein receptor, and can be used interchangeably.

It will be understood by those of ordinary skill in the art that the compounds of the present invention can be homo-multivalent, meaning that the antigen binding moieties bound to the molecular scaffold are all the same, for example, targeting PSMA. However, it is contemplated in the present invention, that the compounds can also be heteromultivalent That is, that the antigen binding moieties bound to the molecular scaffold are not all the same. For example, a compound of the present invention can comprise antigen binding moieties to two or more differing antigens, such as, for example, PSMA and RGD.

In accordance with one or more embodiments of the present invention, the antigen binding moieties used in the compounds of the present invention can include, for example, hepsin, HER-2, ACPP, ADAM10, ADAM15, FN1, FOLH1, GNA12, HRAS, KLK3, MMP3, MMP13, OCLN, SILV, integrins, VEGF, including VEGF1 and VEGF4, Robo-4, MMP2, MMP9, PDGF, TGF-α, and others.

In a further embodiment, the present invention provides a pharmaceutical composition comprising a compound, salt, solvate, or stereoisomer of any one of the compounds as set forth above, and a pharmaceutically acceptable carrier.

In another embodiment, the present invention provides a pharmaceutical composition comprising a compound, salt, solvate, or stereoisomer of any one of the compounds as set forth above, and at least on other biologically active agent and a pharmaceutically acceptable carrier.

In another embodiment, the present invention provides a pharmaceutical composition comprising a compound, salt, solvate, or stereoisomer of any one of the compounds as set forth above, and at least one or more other anticancer compounds, and a pharmaceutically acceptable carrier.

In an embodiment, the present invention provides that the other anticancer compounds can be, for example, anticancer drugs from the following drug classes, including, but not limited to, antimitotics, antineoplastics, antimetabolites, and alkylating agents. Such classes of anticancer drugs are well known in the art.

In an embodiment, the present invention provides methods of imaging PSMA on cells or a population of cells in a subject comprising administering to the subject a compound, salt, solvate, or stereoisomer of any one of the compounds as set forth above, and at least on other biologically active agent and a pharmaceutically acceptable carrier.

In accordance with an embodiment, the present invention provides the use of a compound, salt, solvate, or stereoisomer of any one of the compounds as set forth above, and a pharmaceutically acceptable carrier, in the preparation of a medicament.

In accordance with another embodiment, the present invention provides the use of a compound, salt, solvate, or stereoisomer of any one of the compounds as set forth above, and at least on other biologically active agent and a pharmaceutically acceptable carrier, in the preparation of a medicament.

In accordance with a further embodiment, the present invention provides the use of a compound, salt, solvate, or stereoisomer of any one of the compounds as set forth above, and at least one or more other anticancer compounds, and a pharmaceutically acceptable carrier, in the preparation of a medicament.

EXAMPLES

Solvents and chemicals obtained from commercial sources were of analytical grade or better and used without further purification. All 9-fluorenylmethyloxycarbonyl (Fmoc) protected amino acids including the Fmoc-Lys (Boc)-Wang resin and benzotriazol-1-yloxy)tripyrrolidino-phosphonium hexafluorophosphate (PyBOP) were purchased from Chem Impex International, Inc. (Wooddale, Ill.). Boc-Lys(Azide)-OH was purchased from Anaspec. Carrier-free [$^{111}$In]InCl$_3$ was purchased from MDS Nordion (Ottawa, ON, Canada). DOTANHS-ester (1,4,7,10-Tet-raazacyclododecane-1,4,7,10-tetraacetic acid mono N-hydroxysuccinimide ester) was purchased from Macrocyclics, Inc. (Dallas, Tex.).

Indium (III) nitrate, 2-ethoxy-1-ethoxycarbonyl-1,2-dihydroquinoline (EEDQ), triethylsilane (EtaSiH), N,Ndiisopropylethylamine (DIEA) and triethylamine (TEA) were purchased from Sigma-Aldrich (Saint Louis, Mo.). All other chemicals were purchased from Thermo Fisher Scientific (Pittsburgh, Pa.) unless otherwise specified. Analytical thin-layer chromatography (TLC) was performed using Aldrich aluminum-backed 0.2 mm silica gel Z19,329-1 plates and visualized by ultraviolet light (254 nm), Land 1% ninhydrin in EtOH. Flash chromatography was performed using MP SiliTech 32-63 D 60A silica gel purchased from Bodman (Aston, Pa.). All experiments were performed in duplicate or triplicate to ensure reproducibility. $^1$H NMR spectra were recorded on a Bruker Ultrashield™ 400 MHz spectrometer. Chemical shifts (δ) are reported in ppm downfield by reference to proton resonances resulting from incomplete deuteration of the NMR solvent. Low resolution ESI mass spectra were obtained on a Bruker Daltonics Esquire 3000 Plus spectrometer. High resolution mass spectra were obtained by the University of Notre Dame Mass Spectrometry & Proteomics Facility, Notre Dame, Ind. using ESI by direct infusion on a Bruker micrOTOF-II.

High-performance liquid chromatographic purification of compounds 1-3 were performed using a Phenomenex C$_{18}$ Luna 10×250 mm:column on a Waters 600E Delta LC system with a Waters 486 variable wavelength UV/Vis detector, both controlled by Empower software. For HPLC purification of radiolabeled [$^{111}$In]$_3$, a Waters Novapak Cis 150×3.9 mm; column was used. HPLC was performed using the following methods. Method 1: Solvent A(0.1% TFA in water) and solvent B (0.1% TFA in CH$_3$CN), flow rate 8 mL/min. The elution gradient was 95% A and 5% B for 5 min and 95% A to 50% A and 5% B to 50% B over 5-35 min; Method 2: The elution gradient was 95% A and 5% B for 5 min and 95% A to 70% A and 5% B to 30% B over 5-35 min, Method 3: Solvent A (0.1% TFA in water) and solvent B (0.1% TFA in methanol), flow rate 8 mL/min. The elution gradient was 0-5 min, 77% A and 23% B for 0-5 min, 77% A to 70% A and 23% B to 30% B for 5-35 min, and 70% A to 77% A and 30% B to 23% B for 35 min. Method 4: Solvent A (0.1% TFA in water) and solvent B (0.1% TFA in CH$_3$CN), flow rate 1 mL/min. The elution gradient was 83% A and 17% B for 0-5 min, and 83% A to 70% A and 17% B to 30% B for 5-25 min.

PSMA Inhibition. The PSMA inhibitory activities of 1-3 and [$^{113/115}$In]3 were determined using a fluorescence-based assay according to a previously reported procedure (J Med Chem, 2008; 51:7933-7943). Briefly, lysates of LNCaP cell extracts (25 μL) were incubated with the inhibitor (12.5 μL) in the presence of 4 μM NAAG (12.5 μL) for 120 min. The amount of glutamate released upon hydrolysis of NAAG was measured by incubating with a working solution (50 μL)

of the Amplex Red Glutamic Acid Kit (Life Technologies, Grand Island, N.Y.) for 60 min. Fluorescence was measured with a VICTOR3V multilabel plate reader (Perkin Elmer Inc., Waltham, Mass.) with excitation at 530 nm and emission at 560 nm. Inhibition curves were determined using semi-log plots and $IC_{50}$ values were determined at the concentration at which enzyme activity was inhibited by 50%. Assays Were performed in triplicate. Enzyme inhibitory constants (Ki values) were generated using the Cheng-Prusoff conversion. Data analysis was performed using GraphPad Prism version 4.00 for Windows (GraphPad Software, San Diego, Calif.).

Cell Culture and Animal Models. Sublines of the androgen independent PC-3 human prostate cancer xenograft originally derived from an advanced androgen independent bone metastasis were used. Those sublines have been modified to express high (PC-3 PIP) and low (PC-3 flu) PSMA levels and were generously provided by Dr. Warren Heston (Cleveland Clinic). Both PSMA-expressing (PC-3 PIP) and honexpressing (PC-3 flu) prostate cancer cell lines were grown in RPMI 1640 medium (Mediatech Inc., Manassas, Va.) containing 10% fetal bovine serum (FBS) (Sigma Aldrich, St. Louis, Mo.) and 1% Pen-Strep (Mediatech Inc., Manassas, Va.) as previously described (Clin. Cancer Res. 2008; 14:3036-3043). All cell cultures were maintained at 5% carbon dioxide ($CO_2$), at 37° C. in a humidified incubator. Animal studies were carried out in full compliance with the regulations of the Johns Hopkins Animal Care and Use Committee. Six- to eight-week-old male, non-obese diabetic (NOD)/severe-combined immunodeficient (SCID) mice (Johns Hopkins Animal Core, Baltimore, Md.) were implanted subcutaneously (s.c.) with PC-3 PIP (PSMA+) and PC-3 flu (PSMA−) cells ($2\times10^6$ in 100 µL of Matrigel) at the forward right and left flanks, respectively. Mice were imaged or used in biodistribution assays when the xenografts reached 5 to 7 mm in diameter.

Gamma Scintigraphy and SPECT/CT. Compound [$^{111}$In]3 was imaged using male SCID mice. Xenograft models were generated as described above. Mice were anesthetized using 1% isoflurane in oxygen flowing at 0.6 L/min prior to and during radiochemical injection. Mice were injected via the tail vein with approximately 1.2 mCi (44.4 MBq) of [$^{111}$In]3 formulated in 100 µL of saline, pH 7. After allowing for 30-60 min of radiochemical uptake, anesthetized mice were placed on the scanner gantry and secured with medical tape while the anesthetic flow was increased to 0.8 L/min. The body temperature of the mice was maintained by covering them with several layers of absorbent, disposable pads and illumination with a dissection lamp during scanning. Single-pinhole median-energy (PHME) collimators with an aperture size of 1.0 mm, and stepwise rotation for 64 projection angles in a full 360° rotation, 40 s increments were used for SPECT imaging. The radius of rotation (ROR) was set at 7 cm, which provided a field of view of 7.5 cm to cover the mouse body from head to bladder. A CT scan was performed prior to scintigraphy for both anatomical co-registration and attenuation correction. A total of 512 projections were acquired in a 2 min continuous rotation mode covering a full 360° rotation. Data were reconstructed and fused using commercial software from the vendor (Gamma Medica-Ideas, Northridge, Calif.), which includes a 2D-OSEM algorithm. Data were analyzed and volume-rendered images were generated using AMIDE software (SourceForge, amide.sourceforge.net/).

Biodistribution. PSMA+ PC-3 PIP and PSMA− PC-3 flu xenografts bearing SCID mice were injected via the tail vein with 0.74 MBq (20 µCi) of [$^{111}$In]3. Four mice were sacrificed by cervical dislocation at 2 and 24 h p.i. The heart, lungs, liver, stomach, pancreas, spleen, fat, kidney, muscle, small and large intestines, urinary bladder, and PC-3 PIP and flu tumors were quickly removed. A 0.1 mL sample of blood was also collected. Each organ was weighed, and the tissue radioactivity was measured with an automated gamma counter (1282 Compugamma CS, Pharmacia/LKB Nuclear, Inc., Gaithersburg, Md.). The percentage injected dose per gram of tissue (% ID/g) was calculated by comparison with a standard dilution of the initial dose. All measurements were corrected for radioactive decay Example 1

(3S,7S)-26-Azido-5,13,20-trioxo-4,6,12,21-tetraazahexacosane-1,3,7,22-tetracarboxylic acid, compound 1. This compound was prepared following our previous report (J. Nucl. Med., (SNM Annual Meeting Abstract). 2011; 52 (Supplement 1): 293). Briefly, commercially available Boc-Lys(Azide)-OH was treated with a solution of TFA/$CH_2Cl_2$ (1:1) at ambient temperature for 4 h to remove the Boc group. After solvent removal, the crude product, H-Lys (azide)-OH, was directly used for the next step. To a solution of H-Lys(azide)-OH (50 mg, 0.29 mmol in 500 µL DMSO) was added NHS-ester of Lys-Glu urea (24 mg, 0.43 mmol in 500 µL DMSO) and DIEA (100 µL) and left at ambient temperature for 4 h. Solvent was evaporated to dryness and the residue was dissolved in water and purified by HPLC (Method 1). Retention time (Rt): 17.1 min. 1H NMR (δ, ppm, DMSO): 8.06 (m, 2H), 7.74 (m, 2H), 6.34-6.29 (m, 2H), 4.16-4.03 (m, 3H), 3.00 (m, 2H), 2.33-1.27 (m, 28H). ESI-MS m/Z: 630 [M+H]+.

Example 2

6-amino-2-(2,6-dipropiolamidohexanamido)hexanoic acid, compound 4.

Compound 4 was synthesized using standard Fmoc mediated solid phase peptide synthesis. Formation and masking of free amines was assessed using the Kaiser test. Washing the resin with 3 mL DMF three times, 1 minute each, before and after each step was performed until liberation of the final product from the resin. All steps were performed at ambient temperature unless otherwise mentioned. After being swollen by 3 mL DMF, Fmoc-Lys-(Boc)-Wang resin (500 mg, 0.18 mM) was deprotected by settling with 3 mL 20% piperidine in DMF×2, 5 min each time, before coupling with Fmoc-Lys-(Fmoc)-OH (318 mg, 0.54 mM) preactivated with DIEA (124 uL, 0.72 mM) and PyBOP (280 mg, 0.54 mM in 3 mL DMF). The last coupling was performed twice, 30 minutes in duration each time. The Fmoc groups were removed using 3 mL 20% piperidine in DMF×2, 5 min each time. Coupling with propiolic acid (75 mg, 1.08 mM) was achieved using a solution of EEDQ (268 mg, 1.08 mM) as a coupling reagent in 2 mL DMF and accelerated via exposure to microwave irradiation×5, 30 sec each time. Ten percent of the maximum power of a standard kitchen microwave was enough to achieve complete coupling as indicated by a negative Kaiser test. Cleavage of 4 from the resin was achieved by settling with 2 mL TFA/$H_2O$/TES (95/2.5/2.5) mixture for 30 min followed by washing twice with 2 mL 100% TFA. The collected fractions were evaporated under vacuum after which the concentrated product was purified using a Sep-Pak® Vac 35 cc $tC_{18}$ tube (Waters, WAT043350). Compound 4 was eluted with 5% acetonitrile in water (0.1% TFA). HPLC: Method 2, $R_t$: 10 min. $^1$H NMR (DMSO-ds) (δ, ppm): 8.89 (m, 1H) 8.72 (m, 1H), 8.21

(m, 2H), 7.73 (m, 2H), 4.23 (m, 1H) 4.16-4.10 (m, 4H), 3.04 (m, 2H), 2.77 (m, 2H), 1.74-1.27 (m, 12H). ESIMS m/Z: 379 [M+H]$^+$.

Example 3

(7S)-26-(4-((1-((5-amino-1-carboxypentyl)amino)-1-oxo-6-(1-((7S)-1,3,7,22-tetracarboxy-5,13,20-trioxo-4,6,12,21-tetraazahexacosan-26-yl) 1H-1,2,3-triazole-4-carboxamido)hexan-2-yl)carbamoyl)-1H-1,2,3-triazol-5-yl)-5,13,20-trioxo-4,6,12,21-tetraazahexacosane-1,3,7,22-tetracarboxylic acid, PSMA-targeted homobivalent compound 2

Compound 1 (49 mg, 76.7 µM) and 4 (0.5 eq, 14.5 mg, 38.3 µM) were dissolved in 1 mL H$_2$O/t-BuOH (1/1). To that solution, sodium ascorbate (6 mg, 30 µM) and Cu(OAc)$_2$ (3 mg, 15 µM) were added consecutively, the mixture was purged with N$_2$ gas and stirred at ambient temperature overnight. Compound 2 was purified using Cis SepPak® Vac 2 g column through which the product was successfully eluted using 70/30 water/acetonitrile (0.1% TFA). Compound 2 was further purified by HPLC (Method 1). Rt: 13.9 min, ESI-MS m/Z: 1638 [M+H]$^+$.

Example 4

(7S)-26-(4-((1-((1-carboxy-5-(2-(4,7,10-tris(carboxymethyl)-1,4,7,10-tetraazacyclododecan-1-yl) acetamido)pentyl)amino)-1-oxo-6-(1-((7S)-1,3,7,22-tetracarboxy-5,13,20-trioxo-4,6,12,21-tetraazahexacosan-26-yl)-1H-1,2,3-triazole-4-carboxamido)hexan-2-yl)carbamoyl)-1H-1,2,3-triazol-5-yl)-5,13,20-trioxo-4,6,12,21-tetraazahexacosane-1,3,7,22-tetracarboxylic acid, DOTA conjugated PSMA-targeted homobivalent compound 3

To a solution of 2 (4 mg, 2.44 µM in 500 µL DMF) was added DOTA-NHS ester (1.5 mg, 3.66 µM in 500 µL DML) and DIEA (50 µL) and left at ambient temperature for 4 h. Solvent was removed under vacuum and the residue was dissolved in 2 mL water and was purified using HPLC Method 3. R$_t$: 26.2 min ESIMS m/Z: 2024[M+H], HRESI-MS (m/z): HRESI-MS m/Z: Calcd. for $C_{86}H_{135}N_{22}O_{34}$, 2023.9824; Found 2023.9820.

Example 5

Compound [$^{113/115}$In]3

To a solution of In(NO$_3$)$_3$ (1 mg, 20 µmol in 100 µL) in deionized water was added 3 (1 mg, 0.48 µmol) in 500 µL 0.3 M NaOAc. The resulting solution was heated at 95° C. for 1 h. The solution was purified by HPLC Method 3. The retention time for the product was at 25.8 min. Yield: ~50%. ESIMS m/Z: 1067 [M+H]$^{2+}$.

Example 6

Compound [$^{113}$In]3

For each radiolabeling reaction, approximately 50-70 µg of 3 in 300 mM NaOAc (purged under N$_2$ for 2-3 min) was incubated with 111-148 MBq (3-4 mCi) $^{111}$InCl$_3$ at pH 5.5-6 for 20 h at 95° C. The reaction solution was diluted with 1 mL water. Complexation was monitored by injecting aliquots of 20-40 µL of the solution onto the HPLC. The radiolabeled product [$^{111}$In]3 was obtained in ~70-90% radiochemical yield and the radiochemical purity was >98% as measured by ITLC (Gelman ITLC strips, 10 mM EDTA). HPLC Method 4 was used to purify the radiolabeled product [$^{111}$In]3. Rt: 13.5 min for the desired product and R$_t$: 15.4 min for the free ligand. The specific radioactivity of the agent was ~8.4-204.4 GB/µmol. The acidic eluate was neutralized with 100 µL of PBS solution and the volume of the eluate was reduced under vacuum to dryness. The solid residue was diluted with saline to the desired radioactivity concentration for biodistribution and imaging studies.

Example 7

Figure 2:
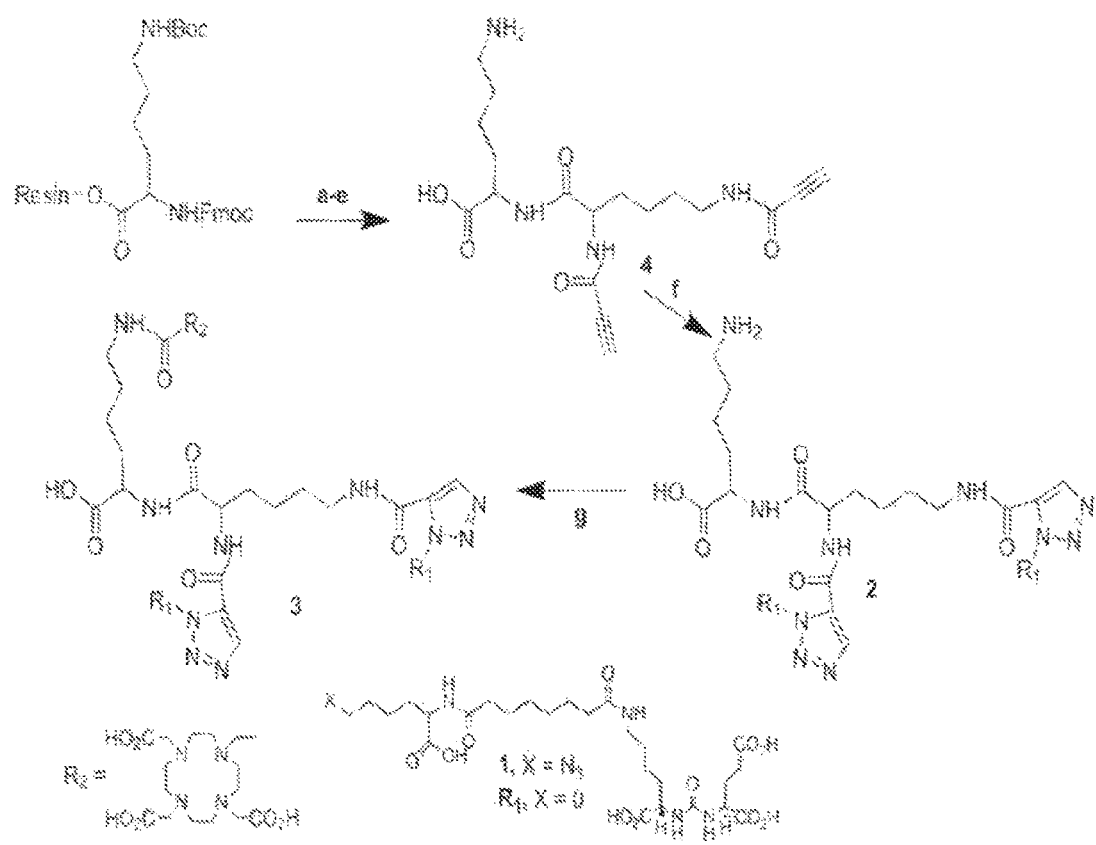
FIG. 2 shows a schematic depiction of the synthesis of compound 3 of the present invention, (a) 20% piperidine in DMF; (b) Fmoc-Lys(Fmoc)-OH, PyBOP, DIEA, DMF; (c) 20% piperidine in DMF; (d) propiolic acid, EEDQ, DMF, microwave irradiation; (e) TFA, $H_2O$, TES; (f) compound I, $Cu(OAc)_2$, Na-Ascorbate, t-BuOH-water; (g) DOTA-NHS, DIEA, DMF

To evaluate the anticipated multivalent effect, a versatile Lys-Glu-urea-based azide intermediate (1) was prepared to serve as a monovalent control compound (FIG. 1) against the bivalent compound 2 and the DOTA-chelated bivalent urea analog, 3 to examine the effect of adding a chelating agent to bivalent urea 2. Compounds 2 and 3 were conveniently prepared by employing simple peptide coupling and click chemistry (Angew Chem Int Ed. 1963; 2:565-598; Angewandte Chemie (International ed.) 2002; 41:2596-2599.) as shown in Scheme 1 (FIG. 2).

Starting with commercially available Fmoc-Lys(Boc)-Wang resin and using standard Fmoc-based solid phase peptide chemistry, 1-4 were prepared in suitable yields. In brief, Fmoc-Lys(Boc)-Wang was treated with 20% piperidine/DMF to remove the Fmoc group followed by coupling with commercially available Fmoc-Lys(Fmoc)-OH in the presence of benzotriazol-1-yloxy)tripyrrolidinophosphonium hexafluorophosphate (PyBOP) and N,N-diisopropylethylamine (DIEA). In the next step, a microwave-assisted coupling reaction was performed using propiolic acid in presence of 2-ethoxy-1-ethoxycarbonyl-1,2-dihydroquinoline (EEDQ) in DMF to improve the yield and purity of the desired product. Finally, 4 was isolated in ~40% yield after treating the resin with a cocktail of TFA/H$_2$O/TES (95/2.5/2.5) at ambient temperature for 0.5 h. Compounds, a Lys-based (α-, ε-) dialkyne peptide, served as the key intermediate to introduce multimerization. Copper catalyzed click chemistry was employed using the azide intermediate 1 and dialkyne peptide 4 to produce multivalent compound 2 in moderate yield after purification by high-performance liquid chromatography (HPLC). Compound 3 was prepared by coupling the free amine of the lysine residue of 2 with the N-hydroxysuccinimide ester of DOTA tris-acid using DIEA as a base in DMSO at ambient temperature for 4 h. Compound 3 was purified by HPLC and obtained in ~15% overall yield. Compound 3 was labeled with $^{111}$In at 95° C. in 0.3 M NaOAc buffer within 20 min in ~70-90% yield and specific radioactivity of ~8.4-204.4 GB/µmol.

Example 8

Figure 3:
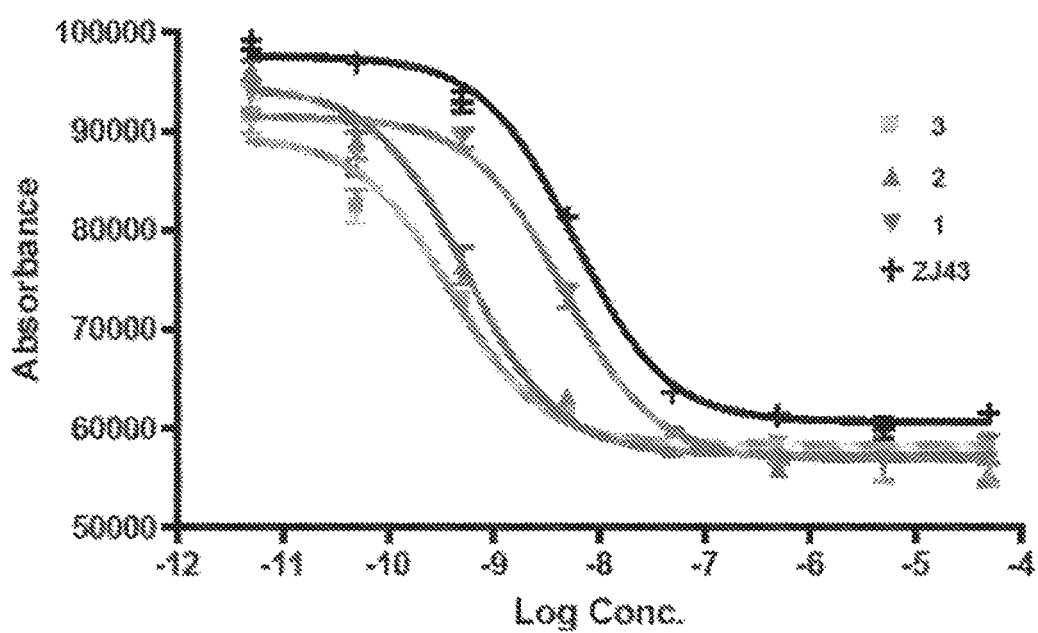
FIG. 3 depicts $IC_{50}$ curves for compounds 1-3 of the present invention.

PSMA inhibition constant (K$_i$) values for 1-3 were determined using a fluorescence-based PSMA inhibition assay. The data are presented in Table 1. As revealed from the Ki values, the binding affinity was found to increase 5-fold from monovalent 1 to bivalent 2. Interestingly, there was an 11-fold increase to the DOTA-chelated bivalent compound 3 compared to 1 leading to subnanomolar binding affinity for 3. Under the same experimental conditions, the Ki value of the known PSMA inhibitor ZJ-43 was 1.16 nM, indicating the high inhibitory potency of 3. The inhibition curves of 1-3, which are expressed with respect to the amount of glutamate released from hydrolysis of the natural PSMA substrate, N-acetylaspartylglutamate (NAAG), are shown in FIG. 3. A structurally similar triazole version of 1, compound 6 (FIG. 1, Table 1) was also tested for PSMA inhibitory activity in vitro. The Ki value of 6 was 0.92 nM in that experiment, in which ZJ-43 demonstrated a Ki value of 0.35 (95% CI, 0.2-0.6 nM), suggesting that the affinity of 6 is likely significantly less than the bivalent compounds 2 or 3. Compound 6 was radiolabeled with 99mTc and its biological properties were tested in vivo. A manuscript describing those biological data is in preparation.

TABLE 1

PSMA Inhibitory activity

| Compound | Ki [nM] | 95% CI of Ki |
|---|---|---|
| 1 | 0.91 | 0.58 nM to 1.45 nM |
| 2 | 0.10 | 0.07 nM to 0.16 nM |
| 3 | 0.08 | 0.05 nM to 0.12 nM |
| ZJ43 | 1.16 | 0.92 nM to 1.46 nM |
| 6 | 0.92* | 0.06 nM to 12 nM |

*separate experiment (see text)

Example 9

Figure 4:
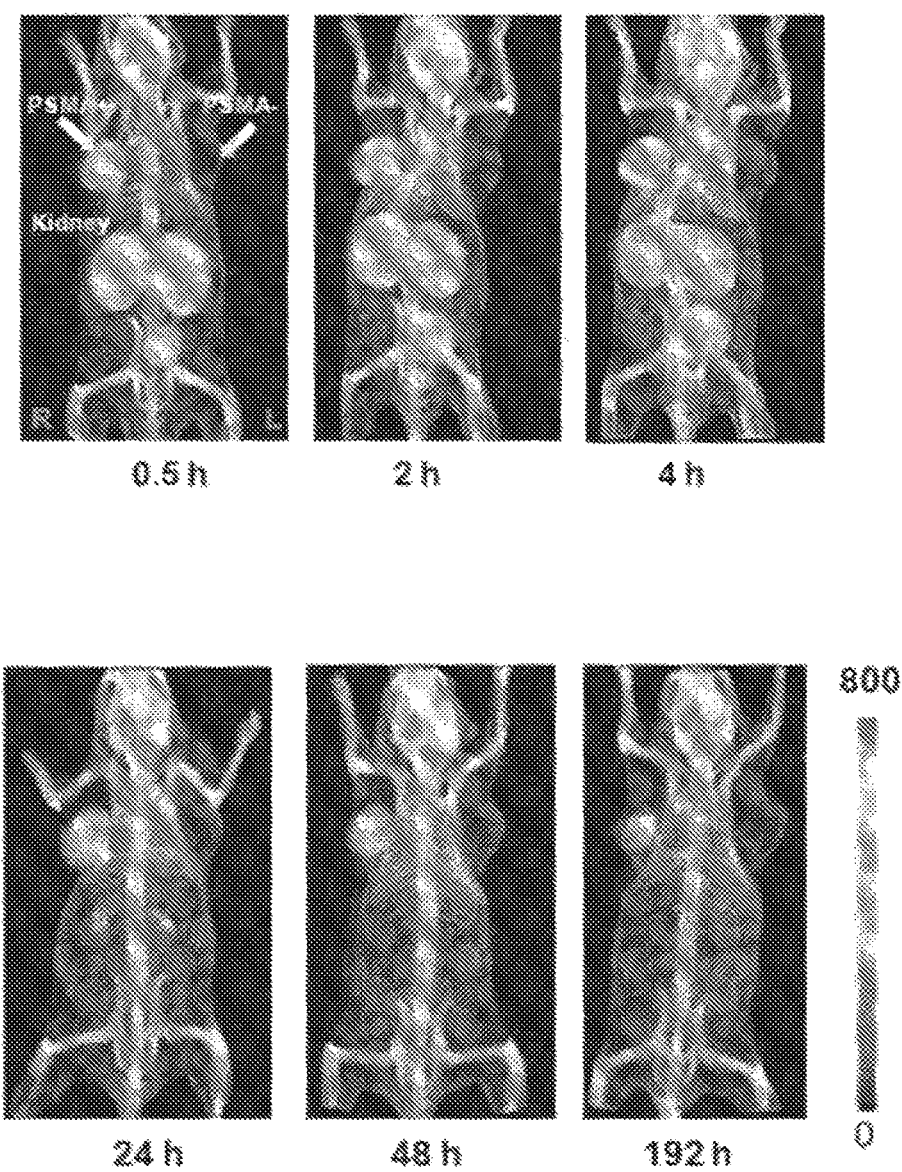
FIG. 4 shows SPECT-CT imaging of [$^{111}$In]3 of the present invention using PSMA+ PIP and PSMA– flu tumors in a male SCID mouse. The mouse was injected intravenously using a single dose of 44.4 MBq (1.2 mCi) of [$^{111}$In]3. Radiochemical uptake was followed up to 192 h post-injection (decay corrected).

FIG. 2 shows the pharmacokinetic behavior of [$^{111}$In]3 in vivo in SCID mice bearing both PSMA+ PC3-PIP and PSMA− PC3-flu xenografts. It was preferred to use the isogenic PSMA+ PIP vs PSMA− flu comparison as the two cell lines are phenotypically identical, differing only in PSMA expression. In this experiment 44.4 MBq (1.2 mCi) of [$^{111}$In]3 was administered intravenously and the animal was imaged repeatedly over an eight day period. Intense radiotracer uptake was seen only in the PSMA+ PIP tumors and in the kidneys. Kidney uptake of the radiotracer is partially due to its route of excretion as well as to specific uptake from the expression of PSMA in mouse kidneys. Clearance of radioactivity from kidney and non-target tissues was more rapid than from target tumor such that by 48 h post-injection (p.i.) a high tumor/background ratio was observed (FIG. 4). Significantly, PSMA+ tumor was possible to image out to eight days p.i. To validate the in vivo imaging data, [$^{111}$In]3 was also assessed for its pharmacokinetics ex vivo. Table 2 shows the percentage injected dose per gram (% ID/g) of radiotracer in selected organs at 2 h and 24 h p.i. Compound [$^{111}$In]3 displayed PSMA-dependent binding in PSMA+ PC3-PIP xenografts with continuous accumulation at the tumor site out to 24 h. We observed tumor uptake values of 31.93±5.87 and 34.03±7.53% ID/g (SEM) at 2 and 24 h, respectively. The blood, spleen, gastrointestinal tract, kidney and bladder displayed the highest uptake at 2 h. Steady clearance from the kidneys was demonstrated, from 168.67±14.12 at 2 h to 66.86±14.22% ID/g at 24 h. The tumor uptake values of [$^{111}$In]3 compare favorably with low molecular weight monovalent PSMA imaging agents [10, 13, 14, 16, 22, 28-31], including N—[N—[(S)-1,3-dicarboxypropyl]carbamoyl]-4-[$^{18}$F]fluorobenzyl-L-cysteine, N—[N—[(S)-1,3-Dicarboxypropyl]carbamoyl]-4-[$^{18}$F]fluorobenzyl-1-cysteine (DCFBC) (Cancer Biol Ther. 2008; 7:974-982), which has recently been administered to human subjects.

TABLE 2

Biodistribution of [$^{111}$In]3

| | 2 hours | 24 hours |
|---|---|---|
| Blood | 0.12 ± 0.04 | 0.02 ± 0.01 |
| Heart | 0.16 ± 0.05 | 0.03 ± 0.01 |
| Lung | 1.84 ± 0.26 | 0.17 ± 0.04 |
| Liver | 0.19 ± 0.03 | 0.16 ± 0.03 |
| Stomach | 0.22 ± 0.07 | 0.03 ± 0.01 |
| Pancreas | 0.43 ± 0.10 | 0.05 ± 0.02 |
| Spleen | 12.33 ± 3.02 | 0.64 ± 0.22 |
| Fat | 0.57 ± 0.17 | 0.19 ± 0.23 |
| Kidney | 168.67 ± 14.18 | 66.86 ± 14.22 |
| Muscle | 0.16 ± 0.08 | 0.03 ± 0.01 |
| Small intestine | 0.10 ± 0.03 | 0.04 ± 0.01 |
| Large intestine | 0.27 ± 0.05 | 0.05 ± 0.03 |
| Bladder | 2.61 ± 1.36 | 0.52 ± 0.27 |
| PC-3 PIP | 31.93 ± 5.87 | 34.03 ± 7.53 |
| PC-3 flu | 0.16 ± 0.03 | 0.09 ± 0.03 |
| PIP: flu | 203 | 379 |
| PIP: blood | 257 | 2,254 |
| PI: muscle | 199 | 1,220 |

Results are expressed as the percentage injected dose per grain (% ID/g) of tissue; n=4

Example 10

Figure 5:
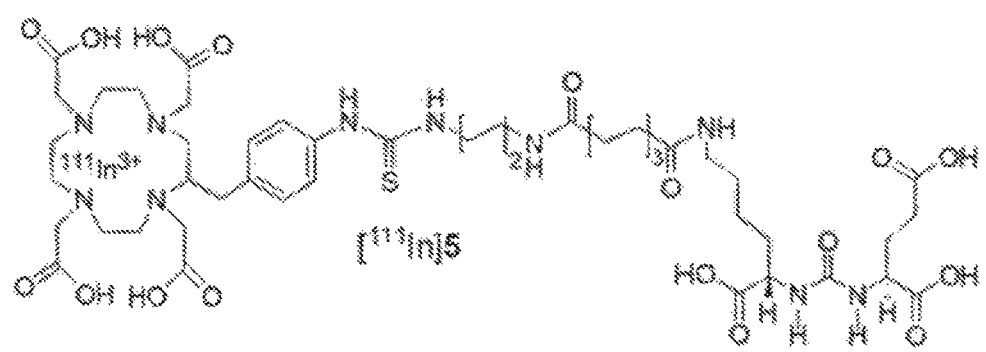
FIG. 5 is the structure of a monovalent compound, [$^{111}$In]5.

The in vivo properties of the bivalent compound [$^{111}$In]3, were also compared with that of one of our lead DOTA-chelated monovalent compounds, [$^{111}$In]5 (FIG. 5) and Table 3). PSMA+ tumor uptake for [$^{111}$In]5 at 2 h p.i. was 29:72±8.09% ID/g, in the same range as that for the bivalent compound [$^{111}$In]3. However at 24 h p.i. monovalent [$^{111}$In]5 showed significantly lower uptake (23.17±3.53% ID/g) than bivalent [$^{111}$In]3 (34.03±7.53% ID/g). At all time points renal retention of [$^{111}$In]5 was significantly lower than that for [$^{111}$In]3. The prolonged tumor retention and rapid clearance from non-target tissues led to very high target to non-target ratios for the bivalent [$^{111}$In]3 at 24 h: PSMA+ PIP to PSMA− flu tumor ratio of 379; tumor to blood ratio of 2,254; and, tumor-to-muscle ratio of 1,220. The corresponding monovalent compound [$^{111}$In]5 demonstrated values of 265, 1,027 and 1,136, in the respective comparisons. The higher uptake and significant retention of [$^{111}$In]3 compared to [$^{111}$In]5 in tumors reflects the advantages of the multimeric design of the former, which affords improved retention in vivo in addition to the anticipated multivalent effects on target binding affinity. One explanation for those results could be that the binding of one PSMA-targeting moiety would significantly enhance the local concentration of the other PSMA-targeting moiety of the homodimer in the vicinity of the active site of PSMA, which may lead to a faster rate of receptor binding or a slower rate of dissociation and translate into higher uptake and longer retention time in the tumor. The apparent increase in molecular size may also prolong circulation time of the dimer and consequently reduce the tumor washout rate.

TABLE 3

Biodistribution of [$^{111}$In]5

| | 2 hours | 24 hours |
|---|---|---|
| Blood | 0.28 ± 0.05 | 0.02 ± 0.01 |
| Heart | 0.16 ± 0.04 | 0.03 ± 0.01 |
| Lung | 1.12 ± 0.32 | 0.10 ± 0.02 |
| Liver | 0.25 ± 0.07 | 0.17 ± 0.02 |
| Stomach | 0.19 ± 0.05 | 0.04 ± 0.01 |
| Pancreas | 0.24 ± 0.05 | 0.04 ± 0.01 |
| Spleen | 4.88 ± 2.63 | 0.32 ± 0.06 |

The invention claimed is:
1. A compound of formula I:

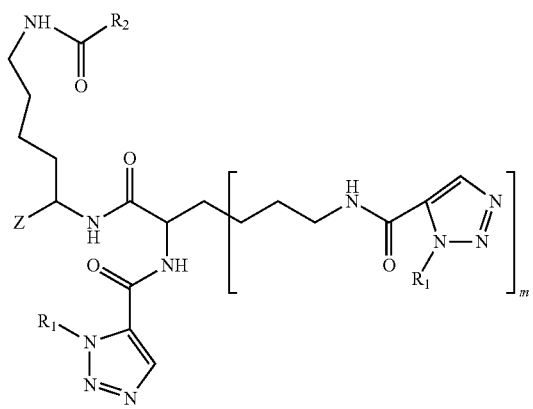

wherein Z is H, CO$_2$H, NH$_2$, SH or OH;
wherein m is 2 to 16;
wherein R$_1$ is the same or different moiety and is selected from the group consisting of:

(III)

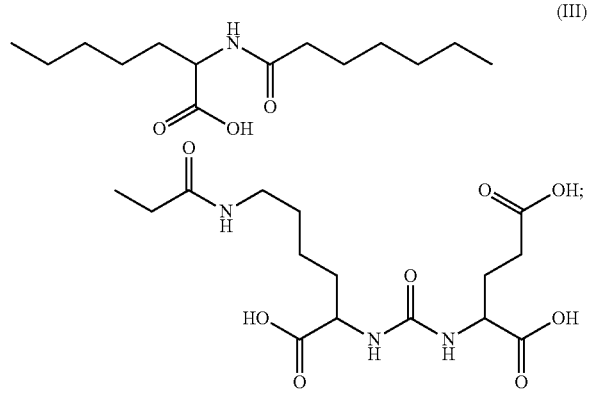

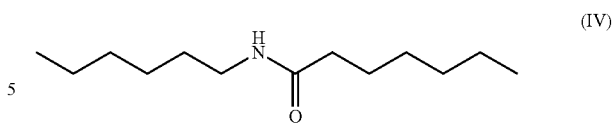

(IV)

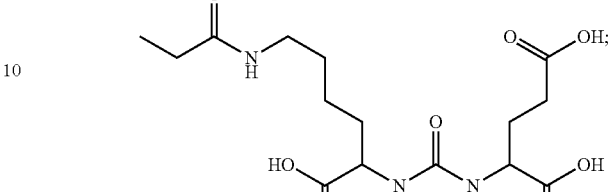

(V)

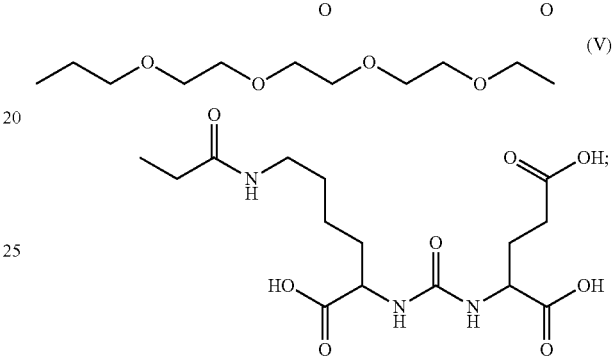

and alternatively, R$_1$ is a peptide ligand to an enzyme or endothelial receptor; and wherein R$_2$ is a chelating moiety, a fluorescent dye or H, wherein when R$_2$ is a chelating moiety, it can be bound to a metal ion useful in imaging, or as a cytotoxic moiety; or a pharmaceutically acceptable salt, solvate, or stereoisomer thereof.

2. The compound of claim, wherein the compound is compound of formula VI:

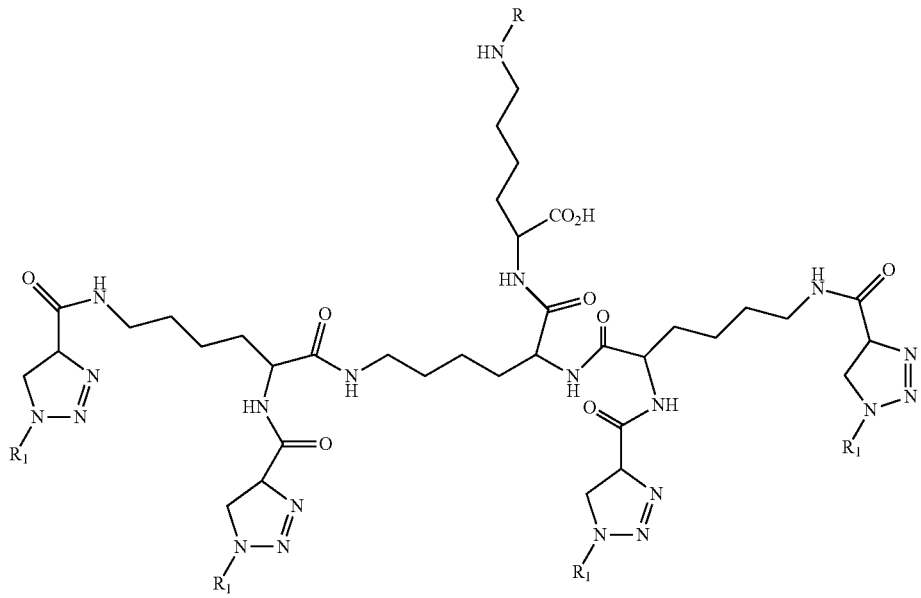

wherein $R_1$ is the same or different moiety and is selected from the group consisting of:

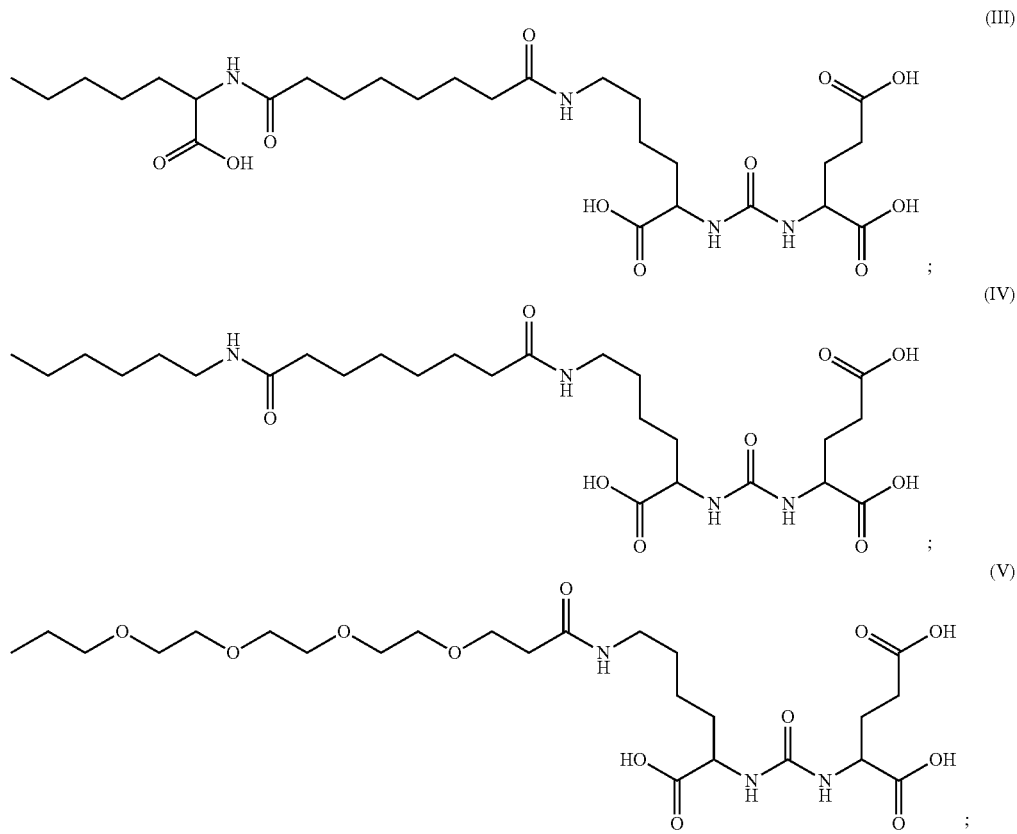

and
alternatively, $R_1$ is a peptide ligand to an enzyme or endothelial receptor; and
wherein $R_2$ is a chelating moiety, a fluorescent dye or H, wherein when $R_2$ is a chelating moiety, it can be bound to a metal ion useful in imaging, or as a cytotoxic moiety; or a pharmaceutically acceptable salt, solvate, or stereoisomer thereof.

3. A pharmaceutical composition comprising a compound, salt, solvate, or stereoisomer of claim 1, and a pharmaceutically acceptable carrier.

4. A pharmaceutical composition comprising a compound, salt, solvate, or stereoisomer of claim 1, and at least one or more other biologically active agents.

5. A pharmaceutical composition comprising a compound, salt, solvate, or stereoisomer of claim 1, and at least one or more other anticancer compounds.

6. A method of imaging prostate cancer in a subject comprising administering to the subject an effective amount of a compound, salt, solvate, or stereoisomer of claim 1, or pharmaceutical compositions thereof, wherein $R_2$ is chelating moiety bound to a metal ion useful in imaging, or fluorescent dye and detecting the prostate by use of PET or SPECT.

7. A compound of formula (XI):

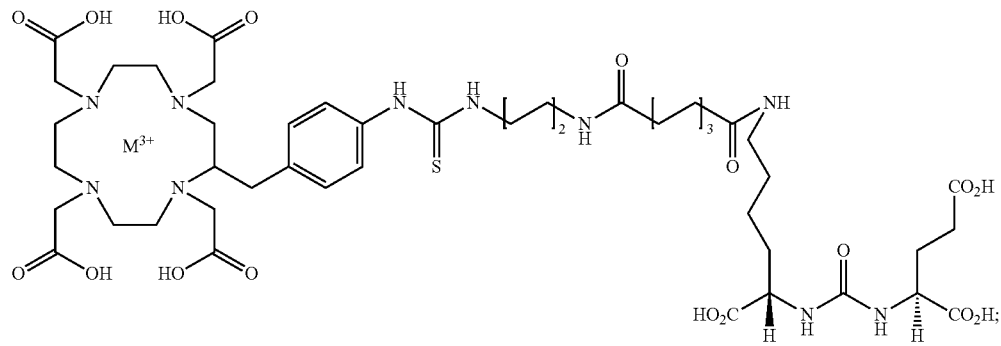

wherein M$^{3+}$ is a metal ion useful in imaging or radiotherapy;

or a pharmaceutically acceptable salt, solvate, or stereoisomer thereof.

8. A pharmaceutical composition comprising a compound, salt, solvate, or stereoisomer of claim 7, and a pharmaceutically acceptable carrier.

9. A pharmaceutical composition comprising a compound, salt, solvate, or stereoisomer of claim 7, and at least one or more other biologically active agent.

10. A pharmaceutical composition comprising a compound, salt, solvate, or stereoisomer of claim 7, and at least one or more other anticancer compound.

11. A method of treating cancer in a subject comprising administering to the subject an effective amount of a compound, salt, solvate, or stereoisomer of claim 7 and wherein the metal ion is useful in radiotherapy.

12. The method of claim 11, wherein the cancer is prostate cancer.

13. A method of imaging prostate cancer in a subject comprising administering to the subject an effective amount of a compound, salt, solvate, or stereoisomer of claim 7, or pharmaceutical compositions thereof and detecting the prostate by use of PET or SPECT.

* * * * *

UNITED STATES PATENT AND TRADEMARK OFFICE
CERTIFICATE OF CORRECTION

PATENT NO. : 9,884,132 B2
APPLICATION NO. : 15/187274
DATED : February 6, 2018
INVENTOR(S) : Martin G. Pomper et al.

It is certified that error appears in the above-identified patent and that said Letters Patent is hereby corrected as shown below:

Column 1, please replace Lines 20-25 with the following:
STATEMENT OF GOVERNMENTAL INTEREST
This invention was made with government support under grant numbers CA134674, CA148901, awarded by the National Institutes of Health. The government has certain rights in the invention.

Signed and Sealed this
Thirteenth Day of November, 2018

Andrei Iancu
*Director of the United States Patent and Trademark Office*